United States Patent
Ko

(10) Patent No.: US 10,443,104 B2
(45) Date of Patent: Oct. 15, 2019

(54) BREAST CANCER SUSCEPTIBILITY GENE GT198 AND USES THEREOF

(71) Applicant: Lan Ko, Augusta, GA (US)

(72) Inventor: Lan Ko, Augusta, GA (US)

(73) Assignee: Lan Ko, Augusta, GA (US)

( * ) Notice: Subject to any disclaimer, the term of this patent is extended or adjusted under 35 U.S.C. 154(b) by 160 days.

(21) Appl. No.: 15/612,536

(22) Filed: Jun. 2, 2017

(65) Prior Publication Data

US 2017/0327900 A1 Nov. 16, 2017

Related U.S. Application Data

(60) Division of application No. 13/921,873, filed on Jun. 19, 2013, now Pat. No. 9,738,936, which is a continuation of application No. 12/763,483, filed on Apr. 20, 2010, now abandoned.

(60) Provisional application No. 61/212,974, filed on Apr. 20, 2009.

(51) Int. Cl.
*C12Q 1/6886* (2018.01)

(52) U.S. Cl.
CPC ..... *C12Q 1/6886* (2013.01); *C12Q 2600/136* (2013.01); *C12Q 2600/156* (2013.01); *C12Q 2600/158* (2013.01)

(58) Field of Classification Search
CPC .................................................... C12Q 1/6886
USPC ............................................................. 435/4
See application file for complete search history.

(56) References Cited

PUBLICATIONS

Ko et al (Molecular and Cellular Biology, 2002, 22(1): 357-369).*

* cited by examiner

*Primary Examiner* — Sean E Aeder

(57) ABSTRACT

It has been discovered that the human GT198 gene (gene symbol PSMC3IP) at chromosome 17q21 acts as a tumor suppressor. The mutation of the GT198 gene causes the increased dominant negative splice variant activity and leads to the loss of wild type GT198 function, and in turn, induces breast and ovarian cancers. One embodiment provides compositions and methods for treating or alleviating one or more symptoms associated with cancer due to the GT198 gene mutations. Another embodiment provides methods and compositions for detecting cancer due to the mutation of the GT198 gene. Still another embodiment provides methods for identifying compounds, antibodies and natural product molecules that are useful for treating cancer due to the mutations of the GT198 gene. Preferably the disclosed compositions antagonize or interfere with the biological activity of splice variants of GT198.

3 Claims, 5 Drawing Sheets

Specification includes a Sequence Listing.

BREAST CANCER SUSCEPTIBILITY GENE GT198 AND USES THEREOF

CROSS-REFERENCE TO RELATED APPLICATIONS

This application is a divisional application of U.S. application Ser. No. 13/921,873, filed Jun. 19, 2013, which is a continuation of U.S. application Ser. No. 12/763,483, filed Apr. 20, 2010, which claims priority to and benefit of U.S. Provisional Patent Application No. 61/212,974 filed on Apr. 20, 2009, and is incorporated herein by reference in its entirety.

REFERENCE TO SEQUENCE LISTING

The Sequence Listing submitted Jun. 2, 2017 as a text file named "KOLAN_DIV_SL.txt," created on Jun. 2, 2017, and having a size of 13,970 bytes is hereby incorporated by reference pursuant to 37 C.F.R. § 1.52(e)(5).

FIELD OF THE INVENTION

Aspects of the invention are generally related to the field of molecular biology, gene diagnostics, and gene therapy.

BACKGROUND OF THE INVENTION

Cancer is an often fatal disease that affects a significant portion of the population. The National Cancer Institute estimated that the age-adjusted death rate due to cancer in the U.S. was 192.7 per 100,000 men and women per year. In January of 2003 approximately 10.5 million Americans had a history of cancer. Breast cancer is the most common malignancy in women, and is a major cause of mortality in women over 45 years of age, especially in United States. Each year over 185,000 new cases are diagnosed and more than 40,000 women die of the disease. However, only a very small percentage of breast and ovarian cancers is attributable to the inheritance of mutations in cancer susceptibility genes such as BRCA1 and BRCA2. The majority of breast and ovarian cancers require the knowledge of additional breast cancer genes for the diagnosis and treatment.

Cancer is a group of diseases characterized by uncontrolled growth and spread of abnormal cells. If the spread is not controlled, it can result in death. Cancer is caused by both external factors (tobacco, chemicals, radiation, and infectious organisms) and internal factors (inherited mutations, hormones, immune conditions, and mutations that occur from metabolism). The regulation of gene expression involved in cancer development has been heavily investigated, but therapeutics and methods for detecting cancer are still needed. Germline mutations in the BRCA1 and BRCA2 genes account for increased susceptibility to familial breast and ovarian cancers (Nathanson, K. L., et al., *Nat Med,* 7:552-6 (2001)). BRCA1 encodes an 1863-amino acid protein with an N-terminal RING domain facilitating ubiquitination and a C-terminal BRCT domain stimulating transcriptional activation (Welcsh, P. L., et al., *Trends Genet,* 16:69-74 (2000)). The BRCT domain induces the cleavage of RNA polymerase II upon ionizing radiation (Bennett, C. B. et al., *PLoS ONE,* 3:e1448 (2008)). The sequence encoded by the large exon 11 of BRCA1 binds to Rad51, a protein critical for homologous recombination and DNA-damage response (Chen, J. J., et al., *Cancer Res,* 59:1752s-1756s (1999)). Alternative splicing variants of BRCA1, such as BRCA1delta11b and BRCA1-IRIS (Wilson, C. A. et al., *Oncogene,* 14:1-16 (1997); ElShamy, W. M. & Livingston, D. M., *Nat Cell Biol,* 6:954-67 (2004)), have been identified with potential functional impact on BRCA1.

BRCA2 encodes a 3418-amino acid protein and has a very similar tissue expression pattern to BRCA1 (Chodosh, L. A., *J Mammary Gland Biol Neoplasia,* 3:389-402 (1998)). Its large exon 11 encodes eight sequence repeats called the BRC repeats, six of which interact with Rad51 (Bork, P., Blomberg, N. & Nilges, M., *Nat Genet,* 13:22-3 (1996); Bignell, G., et al., *Hum Mol Genet,* 6:53-8 (1997); Davies, A. A. et al., *Mol Cell,* 7:273-82 (2001)). Crystal structure analysis demonstrated that the BRC repeat mimics a motif between the interfaces of Rad51 oligomerization (Pellegrini, L. et al., *Nature,* 420:287-93 (2002)), and that the binding of BRCA2 to Rad51 is essential for both functions (Gudmundsdottir, K. & Ashworth, A., *Oncogene,* 25:5864-74 (2006)). The BRCA2 transcripts also undergo complex alternative splicing, and its splicing products are far from defined due to its large gene size (Speevak, M. D., et al., *Eur J Hum Genet,* 11:951-4 (2003); Bieche, I. & Lidereau, R., *Cancer Res,* 59:2546-50 (1999)).

The close functional relationship between BRCA1 and BRCA2 suggests the involvement in DNA-repair pathways in breast and ovarian cancers. However, the specific risk to breast and ovarian cancers that are evidently linked to hormone regulation has not been adequately explained. In addition, early linkage analysis at the chromosome 17q21 locus has provided substantial evidence for breast and ovarian cancer predisposition that is inherited in a Mendelian fashion in families with early onset cancers (Hall, J. M. et al., *Science,* 250:1684-9 (1990); Hall, J. M., et al., *Am J Hum Genet,* 50:1235-42 (1992); Narod, S. A., et al., *Lancet,* 338:82-3 (1991)). However, the BRCA1 mutations explained only a proportion of families with 17q21 association (Nathanson, K. L., et al., *Nat Med,* 7:552-6 (2001); Miki, Y., et al., *Science,* 266, 66-71 (1994)). This paradoxical phenomenon led to the speculation of the presence of an additional candidate gene within the BRCA1 locus (Vogelstein, B. & Kinzler, K. W., *Cell,* 79:1-3 (1994)). In 1995, during refined locus mapping near BRCA1 at 17q21, GT198 (genomic transcript 198, gene symbol PSMC3IP, also known as TBPIP or Hop2) was identified as a cDNA clone (Rommens, J. M., et al., *Genomics,* 28:530-42 (1995)). GT198 was later characterized as a nuclear receptor coregulator that interacts with nuclear receptors and is involved in estrogen, androgen and progesterone receptor-mediated gene regulation (Ko, L., et al., *Mol Cell Biol,* 22, 357-69 (2002); Satoh, T., et al., *Endocrinology,* 150:3283-90 (2009)). GT198 was also found to be homologous to yeast Hop2 (Petukhova, G. V., et al., *Dev Cell,* 5:927-36 (2003)), to interact with Rad51 and to stimulate DNA strand exchange in homologous recombination (Enomoto, R., et al., *J Biol Chem,* 281:5575-81 (2006); Pezza, R. J., et al., *Genes Dev,* 21:1758-66 (2007); Enomoto, R., et al., *J Biol Chem,* 279:35263-72 (2004)).

Existing BRCA1 and BRCA2 genes for detecting breast and ovarian cancer and treating cancer are typically insufficient, especially for a large amount of sporadic cancers.

Thus, it is an object of the invention to provide methods and compositions for the early detection or diagnosis of cancer, for example breast and ovarian cancer.

It is another object of the invention to provide compositions and methods for the treatment of one or more symptoms associated with cancer.

It is still another object to provide methods for screening for chemical compounds and small biological molecules such as antibodies that inhibit or alleviate pathologies due to cells having one or mutations resulting in cancer.

It is another embodiment to provide biomarkers for the detection and diagnosis of cancer.

SUMMARY OF THE INVENTION

GT198 and alternative splice variants thereof are useful biomarkers for the detection and diagnosis of cancer, preferably ovarian and breast cancer. It has been found that the GT198 gene at 17q21 has striking similarities to BRCA1 in its regulation and in function. One embodiment provides a method for detecting or assisting in the diagnosis of cancer by determining the presence of one or more mutations, alterations, or rearrangments of the GT198 gene in a biological sample obtained from a subject. In certain embodiments, the determining step is done by contacting the sample with a probe specific for the one or more mutations, alterations, or rearrangements of the GT198 gene or GT198 gene product to form a detectable complex between the probe and the GT198 gene or gene product. The presence of the detectable complex in the biological sample is indicative of cancer. Preferred mutations in GT198 include, but are not limited to a substitution in exon 4 of GT198, a mutation at nucleotide 85 of exon 4, a mutation at nucleotide 88 of introns 4 of GT198, or a mutation at nucleotide 31 of the 5' untranslated region of GT198. Preferred GT198 variants include but are not limited to GT198a, GT198-1, GT198-2, GT198-3, GT198-4, and GT198a-4.

Another embodiment provides methods and compositions for detecting cancer due to gene mutations and copy number losses in GT198 or cells containing increased splice variants of GT198 protein. The GT198 mutations can be detected using PCR, conformation-sensitive gel electrophoresis and direct sequencing approaches. The copy number changes can be detected by quantitative real-time PCR, southern blotting, and genomic walking, fluorescent in situ hybridization methods. An exemplary method for detecting GT198 variant protein expression in cancer tissues includes, but is not limited to immunohistochemistry analysis. The detection of one or more GT198 mutation that increases the variant expression of GT198 is indicative of cancer.

Another method for diagnosing or assisting in the diagnosis of cancer includes determining cytoplasmic expression levels of GT198 in a sample obtained from a subject by contacting the sample with a probe specific for GT198 to form a detectable complex between the probe and the GT198 gene or gene product, wherein elevated cytoplasmic expression levels of GT198 relative to a control is indicative of cancer.

Still another embodiment provides methods for treating cancer using biological molecules that inhibit, reduce, block or prevent GT198 and GT198 variant protein from functioning. Alternatively, these compounds can reduce or inhibit the bioavailability of GT198 or variants thereof. Preferably the disclosed compositions antagonize or interfere with biological activity of GT198 and/or its alternative splicing variants including GT198a in cells with ectopic expression of GT198 variant proteins.

Another embodiment provides a method for screening of synthetic or natural compounds that inhibit the activity of GT198 or an alternatively spliced variant thereof. The method includes screening of antibodies or small nucleic acid molecules as such siRNA, microRNA, aptamer, and peptide nucleic acid to inhibit the activity of GT198 or alternatively spliced variants.

Kits are also provided. An exemplary kit includes a container containing a nucleic acid probe having at least 10 nucleotides that hybridize under stringent conditions to a nucleic acid encoding a GT198 variant protein and does not hybridize under stringent conditions to a nucleic acid encoding wild-type GT198 protein.

DETAILED DESCRIPTION OF THE INVENTION

Figure 1A:
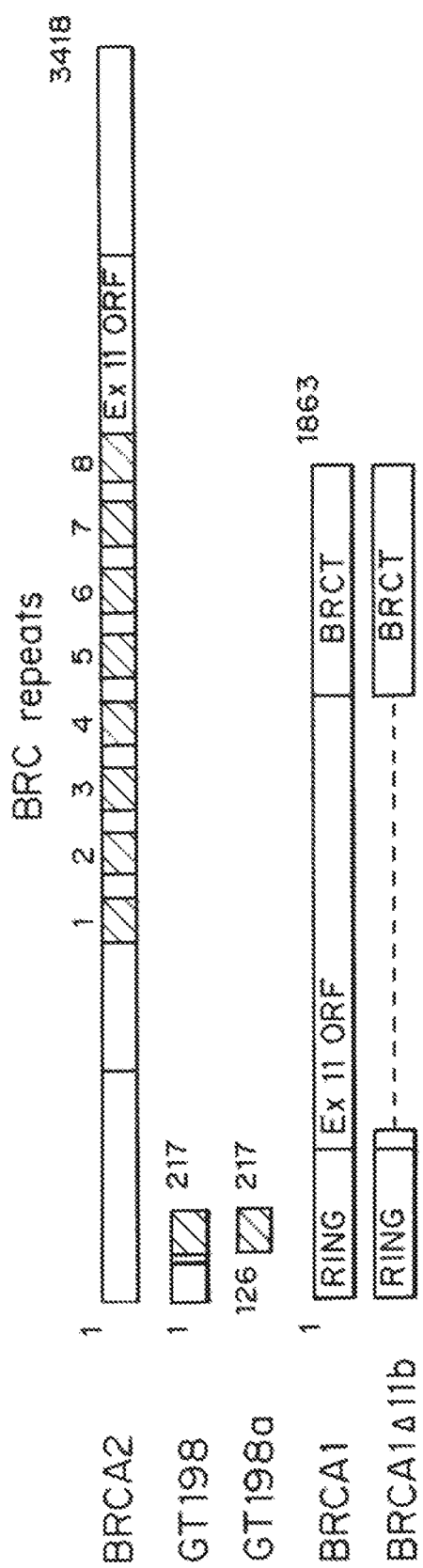
FIG. 1a is schematic representation of BRCA1, variant BRCA1delta11b, BRCA2, GT198, and variant GT198a structures in which the BRC repeat-containing sequences are shown as black boxes. GT198 N-terminal and leucine zipper domains are shown as open boxes.

I. Diagnostics for and Methods of Diagnosing Cancer

GT198 and alternative splice variants thereof are useful biomarkers for the detection and diagnosis of cancer, preferably ovarian and breast cancer. Antagonists of biological activity or bioavailability of GT198 and variants thereof can be used to treat one or more symptoms of cancer. In one embodiment, cytosolic expression of GT198 is indicative of cancer. In another embodiment, expression of a GT198 splice variant is indicative of cancer. Preferred GT198 variants include, but are not limited to GT198a, GT198-1, GT198-2, GT198-3, GT198-4, and GT198a-4. Compositions for treating cancer can be identified by screening for compounds that inhibit the biological activity of GT198 or variants thereof.

A. GT198

GT198 was originally identified as a transcript when the BRCA1 locus was searched for additional breast cancer genes (Rommens, J. M., et al., *Genomics,* 28:530-42 (1995)). The GT198 gene is located 470 Kb proximal and downstream to BRCA1, and 15 Kb distal to HSD17B1, which is one of the most closely linked markers identified during early linkage analysis before positional cloning of BRCA1 (Anderson, L. A., et al., *Genomics,* 17:618-23 (1993); Black, D. M., et al., *Am J Hum Genet,* 52:702-10 (1993)). The human GT198 gene is located between HSD17B1 and BRCA1 genes at chromosome 17q21. It is 15 Kb distal to HSD17B1 and 470 Kb proximal to BRCA1. Mammalian GT198 spans 5 Kb and encodes a 217-amino acid protein containing an N-terminal domain and a C-terminal DNA-binding domain (DBD) (Enomoto, R., et al., *J Biol Chem,* 279:35263-72 (2004)), linked by a leucine zipper domain required for GT198 dimerization and protein interaction (Ko, L., et al., *Mol Cell Biol,* 22, 357-69 (2002)).

The primary sequence of GT198 shares homology with the BRC repeats in BRCA2 which provides strong evidence for its interaction with Rad51. Endogenous expression of GT198 protein closely parallels that of BRCA1 and BRCA2, which suggests they may function in the same pathways. GT198 has dual transcriptional start sites, a feature also presents in BRCA1, permitting differential expression of the wild type and its splice variant transcripts. GT198 variants encode a truncated protein containing the BRC repeat homology and inhibit wild type GT198 activity. Normal stem cell differentiation is accompanied with decreased variant and increased wild type expression in both GT198 and BRCA1. Ectopic expression of GT198 variants, however, induces apoptosis, blocks Rad51 foci formation and is found in cytoplasm of cells in primary breast and ovarian cancer tissues when hundreds of cases were analyzed by immunohistochemistry. Consistent with the above, variant BRCA1delta11b of BRCA1 was known to express in cytoplasm in breast cancers (Wilson, C. A., et al., *Oncogene,* 14, 1-16 (1997)). Furthermore, it is now been found that germline mutations of GT198 in early onset familial breast cancer patients. One of them with onset at age of 33 years has a nonsense mutation generating a premature stop codon that will prevent the expression of full length GT198 but permit the expression of GT198 variant. The same mutation was also carried by her sister with breast cancer onset at age of 40. Together, it suggests that GT198 activity is regulated through its alternative splicing variant. The increased splice variant activity of the GT198 gene may be involved in cancer initiation. GT198 is a novel breast and ovarian cancer susceptibility gene potentially also contributing to 17q21-associated cancer predisposition.

GT198 is a small protein capable of forming a homo- and heterodimer and interacting with DNA-binding proteins including the zinc finger domains of nuclear receptors and Rad51. The dual function of GT198 in transcription and DNA repair mirrors that of BRCA1 and BRCA2. Since BRCA1 contains a C-terminal domain directly modifying RNA polymerase II in transcription (Bennett, C. B. et al., *PLoS ONE,* 3:e1448 (2008)), and has been shown function as a nuclear receptor coactivator, the transcriptional activity of GT198 may be mediated by BRCA1 when they work in concert. In contrast, the hormone-induced activity of BRCA1 in breast and ovarian cancers is potentially through nuclear receptor-associated GT198. A plausible model for GT198 as a partner for BRCA1 would explain their coexpression in tissues, their coordinated regulation in stem cell differentiation, their involvement in both transcription and DNA repair pathways, and their alteration in breast and ovarian cancers. Previous evidence supports the equal involvement of both steroid hormone regulation and DNA repair activity in breast and ovarian cancer initiation.

Alternative splicing control is an integral step in pre-mRNA transcription, and more than 90% of multi-exon genes in the human genome are alternatively spliced (Pan, Q., et al., *Nat Genet,* 40:1413-5 (2008)). Splicing variants influence wild type activities in normal development and cellular differentiation. Splicing defects are frequently found in disease or cancer (Kalnina, Z., *Genes Chromosomes Cancer,* 42:342-57 (2005); Venables, J. P., *Bioessays,* 28:378-86 (2006)). Mutation screening of BRCA1 and BRCA2 showed thousands of changes (Meindl, A., *Int J Cancer,* 97:472-80 (2002)), many of which may alter alternative splicing (Brose, M. S., et al., *Genet Test,* 8:133-8 (2004)). The allelic sequence loss and rearrangement at distant enhancers or at the promoter region of BRCA1 may also affect its alternative splicing regulation (Orban, T. I. & Olah, E., *Mol Pathol,* 56:191-7 (2003)). Multiple splicing variants of GT198 lead to the same functional consequence. If this phenomenon is also present in BRCA1, the wild type BRCA1 activity could be controlled by a variety of its variants. Differential expression of wild type and variant transcripts can be accomplished via two transcriptional start sites, which alternate the usage during early stem cell differentiation and are similarly observed in GT198 and BRCA1. An increased expression of wild-type BRCA2 is also found during stem cell differentiation, although the BRCA2 variants are less well characterized. Consistently, the variant to wild type switch is present in the previously characterized oncogene CoAA suggesting the essential role of alternative splicing in stem cell differentiation (Brooks, Y. S., et al., *J Biol Chem,* 284:18033-46 (2009); Yang, Z., et al., *Nucleic Acids Res,* 35:1919-1932 (2007)). Since splicing forms are competitively expressed, and often functionally counteract, the down-regulation of variants permits an up-regulation of wild types. In contrast, aberrant up-regulation of variants, caused by a wide range of mutations, could be phenotypically equivalent to its wild-type deficiency, i.e., a "loss of tumor suppressor". This will prevent normal cell differentiation when GT198 or BRCA1 is required.

Early evidence from genetic linkage studies demonstrated the close association of familial breast cancers equal to BRCA1 and to HSD17B1 markers (Hall, J. M., et al.,

*Science,* 250:1684-9 (1990); Hall, J. M., et al., *Am J Hum Genet,* 50:1235-42 (1992); Anderson, L. A., et al., *Genomics,* 17:618-23 (1993); Black, D. M., et al., *Am J Hum Genet,* 52:702-10 (1993); Easton, D. F., Bishop, D. T., et al., *Am J Hum Genet* 52:678-701 (1993)), the latter encodes 17-hydroxysteroid dehydrogenase. Since mutations were not identified within the HSD17B1 gene in linked families (Simard, J., et al., *Hum Mol Genet,* 2:1193-9 (1993)), the effort was later focused on the BRCA1 marker. The cloning of BRCA1 was based on the linkage of the families to the D17S1321 and D17S1325 region which flanks BRCA1 but excludes the HSD17B1 and GT198 genes (Miki, Y., et al., *Science,* 266:66-71 (1994); Neuhausen, S. L., et al., *Hum Mol Genet,* 3:1919-26 (1994)). GT198 has a small gene size at 5 Kb near HSD17B1 and was thus missed in the historical candidate gene identification. Subsequent studies showed limited involvement of BRCA1 mutations in 17q21-associated cancer families leading to the speculation of additional unidentified candidate within the BRCA1 locus (Vogelstein, B. & Kinzler, K. W., *Cell,* 79:1-3 (1994)). In view of the functional and genetic evidence of GT198 as described herein, GT198 is potentially another breast cancer susceptibility gene at chromosome 17q21 locus.

There is another possible reason for GT198 not being genetically identified in past investigations of sporadic breast and ovarian cancers. Most genetic analyses for somatic mutations relied on tumor mass but not on rare cancer-initiating cells. One emerging hypothesis, still under debate, is that tumor cells do not grow out of cancer-initiating cells carrying first hit genetic mutation. Instead, tumor growth is influenced by tumor environments containing cancer-initiating cells. If this hypothesis proves true, the genetic alterations in a small percentage of GT198 positive cells are unlikely to be identified from the tumor mass without a visible marker. Thus, the functional analysis comparison of GT198 and BRCA1 might be an essential step towards identifying this candidate that could also be involved in sporadic cancers as supported by its expression patterns in primary tumors.

B. Diagnostics

GT198 variant proteins and nucleic acids encoding them or fragments thereof, can be used in diagnostic assays, screening assays, and in therapeutic applications. In some embodiments, the compositions are used as diagnostic markers for the detection of cancer due to expression of GT198 variants, preferably alternatively spliced variants. Exemplary variants include GT198a, GT198-1, GT198-2, GT198-3, GT198-4, and GT198a-4. Representative cancers include, but are not limited to ovarian and breast cancer. Detection of elevated levels of expression of one or more GT198 variants in tissue or subjects allows for a determination or diagnosis of cancer such as breast and ovarian cancers. The GT198 can be a polypeptide or nucleic acid. To detect or diagnose cancer, baseline values for the expression or activity of GT198 can be established to provide a basis for the diagnosis and/or prognosis of cancer in a subject. Preferred subjects include, mammals including but not limited to humans. In some embodiments, this is accomplished by combining body fluids, tissue biopsies, or cell extracts taken from normal subjects (cancer-free subjects) with one or more antibody(ies) to or nucleic acids that specifically hybridize to a nucleic acid encoding a GT198 variant under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified GT198 variant. Standard values obtained from normal samples may be compared with values obtained from samples from subjects suspected of having cancer. Deviation between standard and subject values establishes the presence of or predisposition to the disease state.

In other embodiments, the expression levels of GT198 splice variants are determined for different cellular states in the cancer phenotype; that is, the expression levels of GT198 variants in cancer-free tissue and in cancer tissue are evaluated to provide expression profiles. An expression profile of a particular cell state or point of development is essentially a "fingerprint" of the state; while two states may have any particular gene or GT198 variant similarly expressed, the evaluation of a number of genes or GT198 variants simultaneously allows the generation of a gene or GT198 variant expression profile that is unique to the state of the cell. By comparing expression profiles of cells in different states, information regarding which genes or GT198 variants are important (including both up- and down-regulation of genes or variants) in each of these states is obtained. Then, diagnosis may be done or confirmed by determining whether or not the tissue from a particular patient has the gene expression profile of normal or cancerous tissue.

"Differential expression," or grammatical equivalents as used herein, refers to both qualitative as well as quantitative differences in the GT198 variant's temporal and/or cellular expression patterns within and among the cells. Thus, a differentially expressed GT198 variant can qualitatively have its expression altered, including an activation or inactivation, in, for example, normal versus ovarian cancer tissue. That is, GT198 variants may be turned on or turned off in a particular state, relative to another state. As is apparent to the skilled artisan, any comparison of two or more states can be made. Such a qualitatively regulated GT198 or variant thereof will exhibit an expression pattern within a state or cell type which is detectable by standard techniques in one such state or cell type, but is not detectable in both. Alternatively, the determination is quantitative in that expression is increased or decreased; that is, the expression of the GT198 variant is either upregulated, resulting in an increased amount of transcript, or downregulated, resulting in a decreased amount of transcript. The degree to which expression differs need only be large enough to quantify via standard characterization techniques as outlined below, such as by use of Affymetrix GeneChip™ expression arrays, Lockhart, *Nature Biotechnology,* 14:1675-1680 (1996). Other techniques include, but are not limited to, quantitative reverse transcriptase PCR, Northern analysis and RNase protection. The change in expression (i.e., upregulation or downregulation) is at least about 50%, more preferably at least about 100%, more preferably at least about 150%, more preferably, at least about 200%, with from 300 to at least 1000% being especially preferred.

As will be appreciated by those in the art, this may be done by evaluation at either the GT198 variant transcript, or the protein level; that is, the amount of gene expression may be monitored using nucleic acid probes to the DNA or RNA equivalent of the GT198 variant transcript, and the quantification of GT198 variant expression levels, or, alternatively, the final GT198 variant product itself (protein) can be monitored, for example through the use of antibodies to the GT198 variant protein and standard immunoassays (ELISAs, etc.) or other techniques, including mass spectroscopy assays, 2D gel electrophoresis assays, etc. Thus, the proteins corresponding to the GT198 variants i.e., those identified as being important in a cancer phenotype, can be evaluated in a cancer diagnostic test.

In some embodiments, antibodies to the GT198 variant can be used in in situ imaging techniques. Preferably the antibody is specific to the GT198 variant polypeptide and does not shown detectable binding to the wild-type GT198 polypeptide. In this method cells are contacted with from one to many antibodies to a GT198 variant polypeptide. Following washing to remove non-specific antibody binding, the presence of the antibody or antibodies is detected. In one embodiment the antibody is detected by incubating with a secondary antibody that contains a detectable label. In another method the primary antibody to the GT198 variant contains a detectable label. In another preferred embodiment each one of multiple primary antibodies contains a distinct and detectable label. This method finds particular use in simultaneous screening for a plurality of cancer markers, for example BRCA1 or BRCA2. As will be appreciated by one of ordinary skill in the art, numerous other histological imaging techniques can be used.

In some embodiments the label is detected in a fluorometer which has the ability to detect and distinguish emissions of different wavelengths. In addition, a fluorescence activated cell sorter (FACS) can be used in the method.

In some embodiments, in situ hybridization of labeled GT198 or GT198 nucleic acid probes to tissue arrays is done. For example, arrays of tissue samples, including cancer tissue and/or normal (cancer-free tissue), are made. In situ hybridization as is known in the art can then be done. Cells having elevated levels of one or more GT198 variants relative to a control are indicative of cancer. An exemplary control includes cells from a subject without cancer.

It is understood that when comparing the expression fingerprints between an individual and a standard, the skilled artisan can make a diagnosis as well as a prognosis. It is further understood that the genes which indicate the diagnosis may differ from those which indicate the prognosis. The data from the disclosed assays can be used to assist in the diagnosis of cancer.

In a preferred embodiment, the GT198 variant proteins, antibodies, nucleic acids are used in prognosis assays. In some embodiments, gene expression profiles can be generated that correlate to cancer severity, in terms of long term prognosis. Again, this may be done on either a protein or gene level, with the use of genes being preferred. In some embodiments, GT198 proteins or nucleic acid probes are attached to solid supports for the detection and quantification of GT198 variant sequences in a tissue or subject. The assays proceed as outlined for diagnosis.

In one embodiment, the presence of wild-type GT198 in the cytosol of cells is indicative of cancer. Typically, antibodies specific to wild-type GT198 can be used in immunological assays of cells or tissue to detect or quantify GT198 in the cytosol. In another embodiment, elevated levels of cytoplasmic expression of wild-type GT198 relative to a control is indicative of cancer.

Another embodiment provides a method for assisting in the diagnosis of cancer by determining expression of GT198 variants in a sample obtained from a subject in combination or alternation with determining the expression of mutations in one or more additional genes. For example, the method can include determining the expression of mutations in BRCA1 or BRCA2 as well as determining the expression of one or more GT198 variants.

C. Efficacy of Therapeutic Agents

The efficacy of therapeutic agents, such as antibodies and/or other candidate drugs also can be determined using the diagnostic assays described above. As will be appreciated by a person of skill in the art, assays to determine the efficacy of a therapeutic agent require the establishment of baseline values. In some embodiments, this is accomplished by combining body fluids, tissue biopsies, or cell extracts taken from a subject with cancer prior to treatment with the candidate drug with one or more antibody(ies) to a GT198 variant under conditions suitable for complex formation. Such conditions are well known in the art. The amount of standard complex formation may be quantified by comparing levels of antibody-target complex in the normal sample with a dilution series of positive controls, in which a known amount of antibody is combined with known concentrations of purified GT198 variant. Standard values obtained from a patient before treatment may be compared with values obtained from a subject after treatment. Deviation between standard and subject values establishes the efficacy of the drug.

II. Screening Assays

In some embodiments, the GT198 variant proteins, antibodies, nucleic acids, and cells containing the GT198 variant proteins or nucleic acids are used in screening assays. For example, screens for agents that modulate the cancer phenotype can be run. This can be done by screening for modulators of gene expression including the expression of GT198 variants or for modulators of GT198 variant protein activity at the individual gene or protein level or by evaluating the effect of drug candidates on a "gene expression profile". In some embodiments, the expression profiles are used in conjunction with high throughput screening techniques to allow monitoring for expression profile genes after treatment with a candidate agent (see Zlokamik, et al., *Science*, 279:84-8 (1998)).

"Modulation" includes both an increase and a decrease in gene expression or activity. The preferred amount of modulation will depend on the original change of the gene expression in normal versus tumor tissue, with changes of at least 10%, preferably 50%, more preferably 100-300%, and in some embodiments 300-1000% or greater. If a gene exhibits a 4 fold increase in tumor compared to normal tissue, a decrease of about four fold is desired; a 10 fold decrease in tumor compared to normal tissue gives a 10 fold increase in expression for a candidate agent is desired, etc.

As will be appreciated by those in the art, this may be done by evaluation at either the variant transcript or the protein level; that is, the amount of GT198 variant expression may be monitored using nucleic acid probes and the quantification of mRNA expression levels, or, alternatively, the level of the gene product itself can be monitored, for example through the use of antibodies to the GT198 variant and standard immunoassays. Alternatively, binding and bioactivity assays with the protein may be done as outlined below.

In some embodiments, gene expression monitoring is done and a number of genes in addition to GT198 variants, i.e. an expression profile, are monitored simultaneously. If desired, multiple protein expression monitoring can be done as well. In embodiments monitoring multiple genes or proteins, the corresponding GT198 variant probes are immobilized to solid supports. It is understood that immobilization can occur by any means, including for example; by covalent attachment, by electrostatic immobilization, by attachment through a ligand/ligand interaction, by contact or by depositing on the surface. "Solid support" or "solid substrate" refers to any solid phase material upon which a GT198 variant sequence, or antibody is synthesized, attached, ligated or otherwise immobilized. A solid support may be composed of organic polymers such as polystyrene, polyethylene, polypropylene, polyfluoroethylene, polyethyleneoxy, and polyacrylamide, as well as co-polymers and grafts thereof. A solid support may also be inorganic, such as glass, silica, controlled-pore-glass (CPG), or reverse-phase silica. The configuration of a solid support may be in the form of beads, spheres, particles, granules, a gel, or a surface. Surfaces may be planar, substantially planar, or non-planar. Solid supports may be porous or non-porous, and may have swelling or non-swelling characteristics. A solid support may be configured in the form of a well, depression or other container, vessel, feature or location. A plurality of solid supports may be configured in an array at various locations, addressable for robotic delivery of reagents, or by detection means including scanning by laser illumination and confocal or deflective light gathering.

Generally, a candidate bioactive agent is added prior to analysis. The term "candidate bioactive agent" or "drug candidate" or grammatical equivalents as used herein describes any molecule, e.g., protein, oligopeptide, small organic or inorganic molecule, polysaccharide, polynucleotide, etc., to be tested for bioactive agents that are capable of directly or indirectly altering either the cancer phenotype, binding to and/or modulating the bioactivity of a GT198 variant, or the expression of a GT198 variant sequence. In a particularly preferred embodiment, the candidate agent suppresses the cancer phenotype, for example to a normal tissue fingerprint. Generally a plurality of assay mixtures is run in parallel with different agent concentrations to obtain a differential response to the various concentrations. Typically, one of these concentrations serves as a negative control, i.e., at zero concentration or below the level of detection. In a preferred embodiment, the expression of one or more GT198 variant is inhibited.

In one aspect, a candidate agent will neutralize the effect of one or more GT198 variant. By "neutralize" it is meant that activity of a protein is either inhibited or counter-acted against so as to have substantially no effect on a cell.

Candidate agents encompass numerous chemical classes, though typically they are organic or inorganic molecules, preferably small organic compounds having a molecular weight of more than 100 and less than about 2,500 daltons. Preferred small molecules are less than 2000, or less than 1500 or less than 1000 or less than 500 D. Candidate agents include functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, proteins, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means. Known pharmacological agents may be subjected to directed or random chemical modifications, such as acylation, alkylation, esterification, amidification to produce structural analogs.

In assays for altering the expression profile of one or more GT198 variant sequences, after the candidate agent has been added and the cells allowed to incubate for some period of time, the sample containing the GT198 variant sequences to be analyzed is added to a solid support. If required, the GT198 variant sequence is prepared using known techniques. For example, the sample may be treated to lyse the cells, using known lysis buffers, electroporation, etc., with purification and/or amplification such as PCR occurring as needed, as will be appreciated by those in the art.

Generally, one of the assay components is labeled to provide a means of detecting the binding complex of interest. By "labeled" herein is meant that a compound has at least one element, isotope or chemical compound attached to enable the detection of the compound. In general, labels fall into three classes: a) isotopic labels, which may be radioactive or heavy isotopes; b) immune labels, which may be antibodies or antigens; and c) colored or fluorescent dyes. The labels may be incorporated into the GT198 variant nucleic acids, proteins and antibodies at any position. For example, the label should be capable of producing, either directly or indirectly, a detectable signal. The detectable moiety may be a radioisotope, such as $^3$H, $^{14}$C, $^{32}$P, $^{35}$S, or $^{125}$I, a fluorescent or chemiluminescent compound, such as fluorescein isothiocyanate, rhodamine, or luciferin, or an enzyme, such as alkaline phosphatase, beta-galacatosidase or horseradish peroxidase. Any method known in the art for conjugating the antibody to the label may be employed, including those methods described by Hunter et al., Nature, 144:945 (1962); David et al., Biochemistry, 13:1014 (1974); Pain et al., J. Immunol. Meth., 40:219 (1981); and Nygren, J. Histochem. and Cytochem., 30:407 (1982)). The label also can be an enzyme, such as, alkaline phosphatase or horseradish peroxidase, which when provided with an appropriate substrate produces a product that can be detected. Alternatively, the label can be a labeled compound or small molecule, such as an enzyme inhibitor, that binds but is not catalyzed or altered by the enzyme. The label also can be a moiety or compound, such as, an epitope tag or biotin which specifically binds to streptavidin. For the example of biotin, the streptavidin is labeled as described above, thereby, providing a detectable signal for the bound target sequence. As known in the art, unbound labeled streptavidin is removed prior to analysis.

As will be appreciated by those in the art, these assays can be direct hybridization assays or can include "sandwich assays", which include the use of multiple probes, as is generally outlined in U.S. Pat. Nos. 5,681,702, 5,597,909, 5,545,730, 5,594,117, 5,591,584, 5,571,670, 5,580,731, 5,571,670, 5,591,584, 5,624,802, 5,635,352, 5,594,118, 5,359,100, 5,124,246 and 5,681,697, all of which are hereby incorporated by reference in their entirety.

A variety of hybridization conditions may be used, including high, moderate and low stringency. The assays are generally run under stringency conditions which allows formation of the label probe hybridization complex only in the presence of target. Stringency can be controlled by altering a step parameter that is a thermodynamic variable, including, but not limited to, temperature, formamide concentration, salt concentration, chaotropic salt concentration pH, organic solvent concentration, etc. To achieve specific hybridization under a variety of conditions, probes specific for GT198 variant polynucleotides are used. The probe is less than about 1000 nucleotides in length, preferably less than 500 nucleotides in length. Preferred probes are preferably at least about 10 nucleotides in length, and most preferably at least about 20 nucleotides in length. Such probes may be used to amplify corresponding GT198 variant sequences from a sample by PCR.

Hybridization may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2.× standard sodium citrate (SSC) (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may include about 0.1% to about 1% SDS. Duration of hybridization is generally less than about 24 hours, usually about 4 to about 12 hours.

These parameters may also be used to control non-specific binding, as is generally outlined in U.S. Pat. No. 5,681,697. Thus it may be desirable to perform certain steps at higher stringency conditions to reduce non-specific binding.

The reactions outlined herein may be accomplished in a variety of ways, as will be appreciated by those in the art. Components of the reaction may be added simultaneously, or sequentially, in any order, with preferred embodiments outlined below. In addition, the reaction may include a variety of other reagents may be included in the assays. These include reagents like salts, buffers, neutral proteins, e.g. albumin, detergents, etc which may be used to facilitate optimal hybridization and detection, and/or reduce non-specific or background interactions. Also reagents that otherwise improve the efficiency of the assay, such as protease inhibitors, nuclease inhibitors, anti-microbial agents, etc., may be used, depending on the sample preparation methods and purity of the target. In addition, either solid phase or solution based (i.e., kinetic PCR) assays may be used.

Once the assay is run, the data is analyzed to determine the expression levels, and changes in expression levels as between states, of GT198 variants, or individual GT198 variant proteins, forming an expression profile.

In some embodiments, screening is done to alter the biological function of the expression product of the GT198 variant. Again, having identified the importance of a variant in a particular state, screening for agents that bind and/or modulate the biological activity of the variant can be run as is more fully outlined below.

In some embodiments, screens are designed to first find candidate agents that can bind to GT198 variant proteins or nucleic acids, and then these agents may be used in assays that evaluate the ability of the candidate agent to modulate the GT198 variant activity and the cancer phenotype. As will be appreciated by those in the art, there are a number of different assays which may be run; binding assays and activity assays.

In some embodiments, binding assays are done. In general, purified or isolated GT198 variant proteins or nucleic acids are used. The methods include combining a GT198 protein or nucleic acids and a candidate bioactive agent, and determining the binding of the candidate agent to the GT198 variant protein or nucleic acids. Generally, the GT198 variant protein or nucleic acids or the candidate agent is non-diffusably bound to a solid support having isolated sample receiving areas (e.g., a microtiter plate, an array, etc.). Microtiter plates and arrays are especially convenient because a large number of assays can be carried out simultaneously, using small amounts of reagents and samples. The particular manner of binding of the composition is not crucial so long as it is compatible with the reagents, maintains the activity of the composition and is nondiffusable. Preferred methods of binding include the use of antibodies (which do not sterically block either the ligand binding site or activation sequence when the protein is bound to the support), direct binding to "sticky" or ionic supports, chemical crosslinking, the synthesis of the protein or agent on the surface, etc. Following binding of the protein or agent, excess unbound material is removed by washing. The sample receiving areas may then be blocked through incubation with bovine serum albumin (BSA), casein or other innocuous protein or other moiety.

In some embodiments, the GT198 variant protein or nucleic acids are bound to the support, and a candidate bioactive agent is added to the assay. Alternatively, the candidate agent is bound to the support and the GT198 variant protein or nucleic acids are added. Novel binding agents include specific antibodies, non-natural binding agents identified in screens of chemical libraries, peptide analogs, aptamers, etc. Of particular interest are screening assays for agents that have a low toxicity for human cells. A wide variety of assays may be used for this purpose, including labeled in vitro protein-protein binding assays, electrophoretic mobility shift assays, immunoassays for protein binding, functional assays (phosphorylation assays, etc.) and the like.

The determination of the binding of the candidate bioactive agent to the GT198 variant protein or nucleic acids may be done in a number of ways. In a preferred embodiment, the candidate bioactive agent is labeled, and binding determined directly. For example, this may be done by attaching all or a portion of the GT198 variant protein or nucleic acids to a solid support, adding a labeled candidate agent (for example a fluorescent label), washing off excess reagent, and determining whether the label is present on the solid support. Various blocking and washing steps may be utilized as is known in the art.

In some embodiments, only one of the components is labeled. For example, the proteins (or proteinaceous candidate agents) may be labeled at tyrosine positions using $^{125}$I, or with fluorophores. Alternatively, more than one component may be labeled with different labels; using $^{125}$I for the proteins, for example, and a fluorophor for the candidate agents.

In some embodiments, the binding of the candidate bioactive agent is determined through the use of competitive binding assays. In this embodiment, the competitor is a binding moiety known to bind to the GT198 variant protein or nucleic acid, such as an antibody, peptide, binding partner, ligand, etc. Under certain circumstances, there may be competitive binding as between the bioactive agent and the binding moiety, with the binding moiety displacing the bioactive agent.

In some embodiments, the candidate bioactive agent is labeled. Either the candidate bioactive agent, or the competitor, or both, is added first to the protein for a time sufficient to allow binding, if present. Incubations may be performed at any temperature which facilitates optimal activity, typically between 4 and 40° C. Incubation periods are selected for optimum activity, but may also be optimized to facilitate rapid high through put screening. Typically between 0.1 and 1 hour will be sufficient. Excess reagent is generally removed or washed away. The second component is then added, and the presence or absence of the labeled component is followed, to indicate binding.

In some embodiments, the competitor is added first, followed by the candidate bioactive agent. Displacement of the competitor is an indication that the candidate bioactive agent is binding to the GT198 variant protein or nucleic acid and thus is capable of binding to, and potentially modulating, the activity of GT198 variant protein or nucleic acid. In this embodiment, either component can be labeled. Thus, for example, if the competitor is labeled, the presence of label in the wash solution indicates displacement by the agent. Alternatively, if the candidate bioactive agent is labeled, the presence of the label on the support indicates displacement.

In other embodiments, the candidate bioactive agent is added first, with incubation and washing, followed by the competitor. The absence of binding by the competitor may indicate that the bioactive agent is bound to the GT198 variant protein or nucleic acid with a higher affinity. Thus, if the candidate bioactive agent is labeled, the presence of the label on the support, coupled with a lack of competitor binding, may indicate that the candidate agent is capable of binding to the GT198 variant protein or nucleic acid.

In some embodiments, the methods include differential screening to identity bioactive agents that are capable of modulating the activity of the GT198 variant protein or nucleic acid. In this embodiment, the methods include combining a GT198 variant protein or nucleic acid and a competitor in a first sample. A second sample comprises a candidate bioactive agent, a GT198 variant protein or nucleic acid and a competitor. The binding of the competitor is determined for both samples, and a change, or difference in binding between the two samples indicates the presence of an agent capable of binding to the GT198 variant protein or nucleic acid and potentially modulating its activity. That is, if the binding of the competitor is different in the second sample relative to the first sample, the agent is capable of binding to the GT198 variant protein or nucleic acid.

In some embodiments, methods for screening for bioactive agents capable of modulating the activity of a GT198 variant protein or nucleic acid in a cell are provided. The methods include adding a candidate bioactive agent, as defined above, to a cell having GT198 variant protein or nucleic acid. Typically, cells having one or more amplicons of GT198 variant are used. Methods for culturing cells and for assaying cell scattering, adhesion and migration are described in Russell et al., *J. Cell Sci.*, 116:3543-3556 (2003), the entire contents of which are incorporated herein by reference.

Positive controls and negative controls may be used in the assays. Preferably all control and test samples are performed in at least triplicate to obtain statistically significant results. Incubation of all samples is for a time sufficient for the binding of the agent to the protein. Following incubation, all samples are washed free of non-specifically bound material and the amount of bound, generally labeled agent determined. For example, where a radiolabel is employed, the samples may be counted in a scintillation counter to determine the amount of bound compound.

A variety of other reagents may be included in the screening assays. These include reagents like salts, neutral proteins, e.g. albumin, detergents, etc which may be used to facilitate optimal protein-protein binding and/or reduce non-specific or background interactions. Also reagents that otherwise improve the efficiency of the assay, such as protease inhibitors, nuclease inhibitors, anti-microbial agents, etc., may be used. The mixture of components may be added in any order that provides for the requisite binding.

In one aspect, the assays are evaluated in the presence or absence or previous or subsequent exposure of physiological signals, for example hormones, antibodies, peptides, antigens, cytokines, growth factors, action potentials, pharmacological agents including chemotherapeutics, radiation, carcinogenics, or other cells (i.e. cell-cell contacts). In another example, the determinations are determined at different stages of the cell cycle process.

III. Pharmaceutical Compositions and Methods of Treatment

A. Pharmaceutical Compositions

Another embodiment provides pharmaceutical compositions containing one or more of antagonists of a GT198 variant protein or nucleic acid. By "pharmacological activity" herein is meant that the compounds are able to inhibit or interfere with the activity of GT198 variant protein or nucleic acid.

The compounds having the desired pharmacological activity may be administered in a physiologically acceptable carrier to a subject or patient. A "subject" or "patient" includes both humans and other animals, particularly mammals, and domestic animals. Thus, the methods are applicable to both human therapy and veterinary applications.

In some embodiments, bioactive agents include antibodies that recognize GT198 variant protein and that have been demonstrated to inhibit or modulate GT198 variant protein activity or bioavailability. In other embodiments, bioactive agents include antisense or siRNA compositions against GT198 intron 1 sequence:

gtaacggcgccgtgggcgcggggaagacccgggagggcagtgggtgag Gaggtcggttgagtggccccctcccctgcctttctctccgtag (SEQ ID NO: 4). These agents can be delivered directly or in pharmaceutical compositions along with suitable carriers or excipients, as well known in the art. Present methods of treatment include embodiments providing for administration of an effective amount of a compound or agent that inhibits the activity or expression of GT198 variant to a patient in need of treatment.

An effective amount of such agents can readily be determined by routine experimentation, as can the most effective and convenient route of administration and the most appropriate formulation. Various formulations and drug delivery systems are available in the art.

Suitable routes of administration may, for example, include oral, rectal, transmucosal, transdermal, nasal, or intestinal administration and parenteral delivery, including intramuscular, subcutaneous, intramedullary injections, as well as intrathecal, direct intraventricular, intravenous, intraperitoneal, intranasal, or intraocular injections. The agent or composition thereof may be administered in a local rather than a systemic manner. For example, a suitable agent can be delivered via injection or in a targeted drug delivery system, such as a depot or sustained release formulation.

The pharmaceutical compositions may be manufactured by any of the methods well-known in the art, such as by conventional mixing, dissolving, granulating, dragee-making, levigating, emulsifying, encapsulating, entrapping, or lyophilizing processes. The compositions can include one or more physiologically acceptable carriers such as excipients and auxiliaries that facilitate processing of active molecules into preparations for pharmaceutical use. Proper formulation is dependent upon the route of administration chosen.

For example, for injection, the composition may be formulated in aqueous solutions, preferably in physiologically compatible buffers such as Hanks's solution, Ringer's solution, or physiological saline buffer. For transmucosal or nasal administration, penetrants appropriate to the barrier to be permeated are used in the formulation. Such penetrants are generally known in the art. For oral administration, the agents can be formulated readily by combining the active agents with pharmaceutically acceptable carriers well known in the art. Such carriers enable the agents of the invention to be formulated as tablets, pills, dragees, capsules, liquids, gels, syrups, slurries, suspensions and the like, for oral ingestion by a subject. The agents may also be formulated in rectal compositions such as suppositories or retention enemas, e.g., containing conventional suppository bases such as cocoa butter or other glycerides.

Pharmaceutical preparations for oral use can be obtained as solid excipients, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active agent doses.

Pharmaceutical preparations for oral administration include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for such administration.

For administration by inhalation, the agents can be conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide, or any other suitable gas. In the case of a pressurized aerosol, the appropriate dosage unit may be determined by providing a valve to deliver a metered amount. Capsules and cartridges for use in an inhaler or insufflator may be formulated. These typically contain a powder mix of the agent and a suitable powder base such as lactose or starch.

Compositions formulated for parenteral administration by injection, e.g., by bolus injection or continuous infusion can be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Formulations for parenteral administration include aqueous solutions of the compound or agent to be administered, including in water-soluble form.

Suspensions of the active agents may also be prepared as appropriate oily injection suspensions. Suitable lipophilic solvents or vehicles include fatty oils such as sesame oil and synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the agents to allow for the preparation of highly concentrated solutions. Alternatively, the active ingredient may be in powder form for constitution with a suitable vehicle, e.g., sterile pyrogen-free water, before use.

As mentioned above, the compositions can also be formulated as a depot preparation. Such long acting formulations may be administered by implantation (for example, subcutaneously or intramuscularly) or by intramuscular injection. Thus, for example, the present agents may be formulated with suitable polymeric or hydrophobic materials (for example as an emulsion in an acceptable oil) or ion exchange resins, or as sparingly soluble derivatives, for example, as a sparingly soluble salt.

Suitable carriers for the hydrophobic molecules of the invention are well-known in the art and include co-solvent systems comprising, for example, benzyl alcohol, a nonpolar surfactant, a water-miscible organic polymer, and an aqueous phase. The co-solvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:SW) consists of VPD diluted 1:1 with a 5% dextrose in water solution. This co-solvent system is effective in dissolving hydrophobic agents and produces low toxicity upon systemic administration. Naturally, the proportions of a co-solvent system may be varied considerably without destroying its solubility and toxicity characteristics. Furthermore, the identity of the co-solvent components may be varied. For example, other low-toxicity nonpolar surfactants may be used instead of polysorbate 80, the fraction size of polyethylene glycol may be varied, other biocompatible polymers may replace polyethylene glycol, e.g. polyvinyl pyrrolidone, and other sugars or polysaccharides may substitute for dextrose.

Alternatively, other delivery systems for hydrophobic molecules may be employed. Liposomes and emulsions are well known examples of delivery vehicles or carriers for hydrophobic drugs. Liposomal delivery systems are discussed above in the context of gene-delivery systems. Certain organic solvents such as dimethylsulfoxide also may be employed, although usually at the cost of greater toxicity. Additionally, the agents may be delivered using sustained-release systems, such as semi-permeable matrices of solid hydrophobic polymers containing the effective amount of the composition to be administered. Various sustained-release materials are established and available to those of skill in the art. Sustained-release capsules may, depending on their chemical nature, release the agents for a few weeks up to over 100 days. Depending on the chemical nature and the biological stability of the therapeutic reagent, additional strategies for protein stabilization may be employed.

For any composition employed herein, a therapeutically effective dose can be estimated initially using a variety of techniques well-known in the art. For example, in a cell culture assay, a dose can be formulated in animal models to achieve a circulating concentration range that includes the $IC_{50}$ as determined in cell culture. Where inhibition of GT198 or GT198 variant activity is desired, the concentration of the test agent that achieves a half-maximal inhibition of GT198 or GT198 variant activity can be determined. Dosage ranges appropriate for human subjects can be determined, using data obtained from cell culture assays and other animal studies.

A therapeutically effective dose of an agent refers to that amount of the agent that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is the therapeutic index, which can be expressed as the ratio $LD_{50}/ED_{50}$. Agents that exhibit high therapeutic indices are preferred.

Dosages preferably fall within a range of circulating concentrations that includes the $ED_{50}$ with little or no toxicity. Dosages may vary within this range depending upon the dosage form employed and the route of administration utilized. The exact formulation, route of administration, and dosage should be chosen, according to methods known in the art, in view of the specifics of a subject's condition.

Dosage amount and interval may be adjusted individually to provide plasma levels or tissue levels of the active moiety which are sufficient to affect the expression or activity of GT198 or GT198 variant, as desired, i.e. minimal effective concentration (MEC). The MEC will vary for each agent but can be estimated from, for example, in vitro data, such as the concentration necessary to achieve 50-90% inhibition of GT198 or GT198 variant activity using the assays described herein. Dosages necessary to achieve the MEC will depend on individual characteristics and route of administration. Agents or compositions thereof should be administered using a regimen which maintains plasma levels above the MEC for about 10-90% of the duration of treatment, preferably about 30-90% of the duration of treatment, and most preferably between 50-90%. In cases of local administration or selective uptake, the effective local concentration of the drug may not be related to plasma concentration.

The amount of agent or composition administered will, of course, be dependent on a variety of factors, including the sex, age, and weight of the subject being treated, the severity of the affliction, the manner of administration, and the judgment of the prescribing physician.

The present compositions may, if desired, be presented in a pack or dispenser device containing one or more unit dosage forms containing the active ingredient. Such a pack or device may, for example, comprise metal or plastic foil, such as a blister pack. The pack or dispenser device may be accompanied by instructions for administration. Compositions comprising a agent of the invention formulated in a compatible pharmaceutical carrier may also be prepared, placed in an appropriate container, and labeled for treatment of an indicated condition. Suitable conditions indicated on the label may include treatment of disorders or diseases, such as breast and ovarian cancers or other cancers and conditions associated with altered expression of GT198.

B. Methods of Treatment

One embodiment provides a method for treating one or more symptoms of cancer by administering an effective amount of an inhibitory nucleic acid specific for a nucleic acid encoding a GT198 variant protein to alleviate one or more symptoms associated with a cancer. The inhibitory nucleic acid can be antisense DNA or siRNA. Symptoms associated with cancer include tumor size and cellular proliferation. Representative cancers that can be treated include, but are not limited to ovarian, prostate and breast cancers. The inhibitory nucleic acid can be one or more of the compositions disclosed above.

The disclosed GT198 or GT198 variant antagonist compositions can be administered to a subject in need thereof alone or in combination with one or more additional therapeutic agents or combinations of the at least two different GT198 antagonists. Representative GT198 or GT198 variant antagonists include, but are not limited to inhibitory nucleic acids such as siRNA and antisense DNA, and antagonistic antibodies or antigen binding fragments thereof. The additional therapeutic agents are selected based on the condition, disorder or disease to be treated. For example, GT198 antagonists can be co-administered with one or more additional agents that function to inhibit GT198 biological function or bioavailability.

The GT198 antagonist can also be combined with one or more additional therapeutic agents. Representative therapeutic agents include, but are not limited to chemotherapeutic agents and pro-apoptotic agents. Representative chemotherapeutic agents include, but are not limited to amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin, docetaxel, doxorubicin, epirubicin, etoposide, fludarabine, fluorouracil, gemcitabine, hydroxycarbamide, idarubicin, ifosfamide, irinotecan, leucovorin, liposomal doxorubicin, liposomal daunorubicin, lomustine, melphalan, mercaptopurine, mesna, methotrexate, mitomycin, mitoxantrone, oxaliplatin, paclitaxel, pemetrexed, pentostatin, procarbazine, raltitrexed, satraplatin, streptozocin, tegafur-uracil, temozolomide, teniposide, thiotepa, tioguanine, topotecan, treosulfan, vinblastine, vincristine, vindesine, vinorelbine, or a combination thereof. Representative pro-apoptotic agents include, but are not limited to fludarabinetaurosporine, cycloheximide, actinomycin D, lactosylceramide, 15d-PGJ(2) and combinations thereof.

IV. Kits

Kits having a container housing a probe that specifically binds to GT198 or GT198 variant proteins or nucleic acids is also provided. The kit can be used to detect the presence of mutation in GT198 indicative of cancer. In one embodiment the probe is antibody specific for GT198 or GT198 variant proteins. The antibody can be monoclonal, polyclonal, single strand, humanized, and chimeric or an antigen binding fragment thereof. In another embodiment the probe is a nucleic acid probe, preferably at least 10 nucleotides in length that specifically binds to a nucleic acid encoding GT198 or a variant thereof. The kit optionally includes probes for detecting one or more biomarkers for cancer. Preferred biomarkers in cancer that can be combined with GT198 marker include mutations in BRCA1 and BRCA2. Thus, nucleic acid probes that specifically hybridize to mutations in BRCA1 and BRCA2 can be included in the kit. Reagents such as buffers and materials to detect hybridization can also be included in the kit.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

EXAMPLES

Methods and Materials

Cloning of GT198 Variants

The presence of human GT198 variants in tissues was initially detected by RT-PCR, followed by sequencing analysis. Full-length GT198-1 to -4 cDNAs containing a longer 5' end similar to that of wild type were subsequently obtained by 5'RACE (Invitrogen). Human and mouse GT198a variant cDNAs were detected from human BG01 cells and mouse P19 stem cells, respectively, both with the retention of the intron 1. Subsequent 5'RACE using intron 1 primer showed a shorter 5' end at the same nucleotide positions in human and mouse sequences almost immediately before their start codons. Human GT198a-4 was identified in tissues using intron 1 specific primers. Expression pattern analysis of P19 stem cells then relied on the specific primer at 5' for the wild type GT198 and the intron 1 primer for variant GT198a. Identified cDNA sequences have been deposited and released in GenBank with accession numbers as follows: hGT198, FJ952179; hGT198-1, FJ952180; hGT198-2, FJ952181; hGT198-3, FJ952182; hGT198-4, FJ952183; hGT198a, GQ851964; hGT198a-4, GQ851965; mGT198, FJ937966; and mGT198a, FJ937967.

RT-PCR and Quantitative PCR Analysis

Endogenous GT198 and its variants were analyzed using first-strand cDNAs from multiple normal human tissues and cancer cell lines (MTC™ panels, Clontech). In stem cells, total RNA was isolated at each differentiation stage using Trizol reagent (Invitrogen), treated with DNase I, reverse-transcribed to cDNA using SuperScript III (Invitrogen), and normalized for their concentrations before RT-PCR. Real-time PCR (iCycler, BioRad) was performed using SYBR Green dye in duplicate in a 25 ul reaction. The results were normalized to GAPDH.

Stem Cell Differentiation

Embryoid body formation from mouse embryonic stem (ES) cells or embryonal carcinoma (EC) P19 cells has been previously described Brooks, Y. S. et al. *J Biol Chem*, 284:18033-46 (2009). Briefly, undifferentiated P19 cells (EC) were induced to differentiate by 500 nM all-trans retinoic acid for 4 days to form embryoid bodies (EB2-4). Total RNA was isolated at each stage of P19 differentiation for RT-PCR analysis. Mouse ES cells were grown on g-irradiated feeder fibroblasts, and were differentiated into embryoid bodies by serum deprivation. ES-derived embryoid bodies were paraffin-embedded for immunohistochemistry analysis.

Luciferase Assay

P19 cells were maintained in alpha-MEM supplemented with 2.5% fetal bovine and 7.5% bovine calf serum. Cells were cultured in 24-well plates and transfected in triplicates using Lipofectamine 2000 (Invitrogen) with MMTV luciferase reporter (100 ng), glucocorticoid receptor (10 ng), and various amounts of GT198 expression plasmids. Cells were incubated with the ligand dexamethasone (100 nM) to induce the MMTV-luciferase reporter, when applicable, for 16 hours before harvest. Relative luciferase activities in were measured by a Dynex luminometer. Data are shown as means of triplicate transfections +/− standard errors.

Immunohistochemistry and Immunofluorescence

Polyclonal anti-GT198 antibody was previously prepared from rabbits (Covance)(Ko, L., et al., *Mol Cell Biol*, 22:357-69 (2002). Recombinant GT198 or its fragments as antigens were cross-linked to the Affi-gel 10 resin (Bio-Rad) for affinity purification. Paraffin-embedded tumor tissues in array format were from Imgenex and US Biomax, Inc. Antibody binding was detected using biotinylated anti-rabbit IgG F(ab)2 secondary antibody followed by detecting reagents (DAKO). Sections were counterstained with hematoxylin. Immunofluorescence double staining was carried out using rabbit anti-GT198 antibody and mouse anti-Flag antibody (Sigma). Cy3- and FITC-conjugated secondary antibodies (Jackson Immuno-Research Laboratory Inc.) were applied at a dilution of 1:200. GFP-Rad51 plasmid contains mouse full-length Rad51 in pEGFP-C3 vector (Clontech). For TUNEL assay, immunofluorescent antibody binding was performed prior to the TUNEL assay using an In Situ Cell Death Detection Kit (Roche). Sections were counterstained with DAPI.

Western Blot Analysis

Endogenous or overexpressed GT198 and its variants were detected by Western blot analysis using whole cell lysate from overexpressed 293 cells or from P19 stem cells Immunoprecipitation was performed using anti-Flag M2 agarose beads (Sigma), incubated with 1:10 diluted cell extracts from transfected cells in binding buffer. The precipitates were washed and subjected to Western blot analysis using anti-GT198 antibodies. The blots were probed with anti-GT198 at a dilution of 1:200 and detected with the ECL system (Amersham Pharmacia).

Whole Mount In Situ Hybridization

Mouse embryos at E8.5, E9.5, and E10.5 were fixed overnight in 4% paraformaldehyde in PBS with 0.1% Tween at 4° C. and dehydrated through a serial methanol at 25%, 50%, 75% and 100%. The dehydrated embryos were treated with RNase-free DNase I (50 U/ml) before hybridization with denatured riboprobe. The antisense and sense riboprobes were produced by in vitro transcription in the presence of Digoxigenin-UTP (Roche Diagnostics), using full-length GT198 cDNA in pcDNA3 vector. Stained embryos were fixed and photographed.

Subjects and Materials

Genomic DNA or RNA was isolated from the Epstein-Barr virus (EBV)-immortalized B-lymphoblastoid cell lines derived from familial breast cancer patients. These patients were diagnosed with breast cancers before age 40 and did not carry a mutation in BRCA1 and BRCA2. Genomic DNA isolated from whole blood was also available to confirm the mutations identified in cells lines. Informed consent from the individuals was obtained following institutional guidelines.

Southern Blot Analysis

Figure 4A:
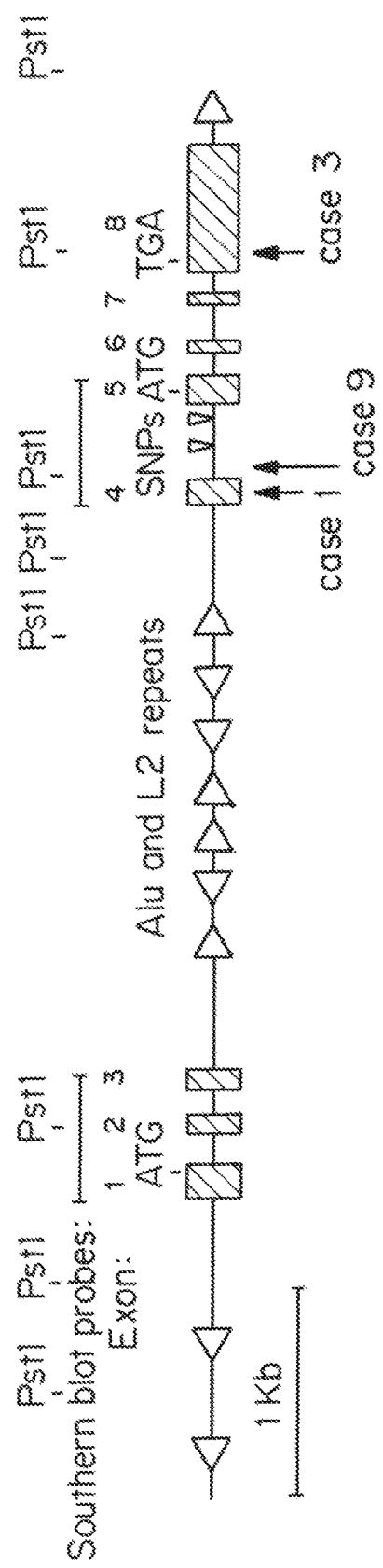
FIG. 4a is a schematic diagram of the GT198 gene. Introns are shown as lines and exons as boxes, Alu and L2 repeats as open orientated triangles, translation start and stop codons are indicated. Filled arrows indicate mutations and open arrows indicate locations of single nucleotide polymorphisms (SNPs).

Genomic DNA (10 ug) isolated from B-lymphoblastoid cell lines of breast cancer patients was digested by restriction enzyme Pst I overnight, separated by 1% agarose gel, transferred to positively charged nylon membrane, and probed with random-primed $^{32}$P-labeled probe (Stratagene). The blot probed by exon 1-3 probe was stripped and re-probed with exon 4-5 probe. Both probes contain small introns as illustrated in FIG. 4a.

Example 1

Protein Sequence Homology Among GT198 and the BRC Repeats in BRCA2

Figure 1B:
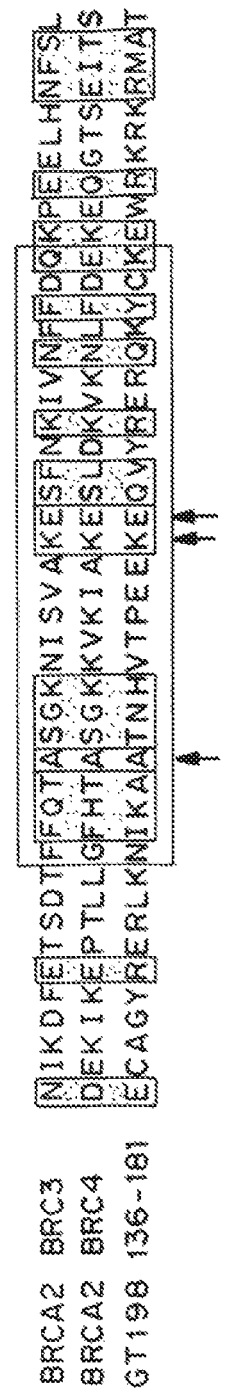
FIG. 1b is a sequence alignment of BRC3 (SEQ ID NO:1) and BRC4 (SEQ ID NO:2) in BRCA2 and GT198 C-terminal domain (SEQ ID NO:3) using ClustalW 2.0.8. Residues with homology to the BRC repeat of BRCA2 are boxed. Identical residues are indicated with an arrow, and the remaining shaded residues are conserved. Number indicates amino acids.
Figure 1C:
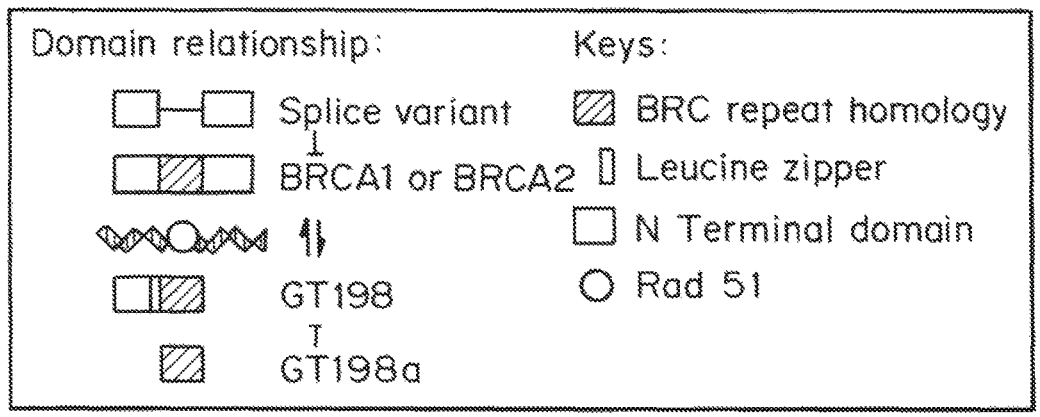
FIG. 1c is a diagram showing that the splice variants of GT198 or BRCA1 or BRCA2 serve dominant negative roles to their wild types. GT198 potentially competes with BRCA2 in Rad51 (circle) interaction.

GT198 has an N-terminal domain and a C-terminal DNA-binding domain (DBD) linked by a leucine zipper dimerization domain. Due to the functional similarities among GT198, BRCA1, and BRCA2 described below, we performed the multiple sequence alignment of BRCA1, BRCA2, and GT198 using ClustalW, and identified that the C-terminal DBD of GT198 is homologous to the BRC repeats in BRCA2 (FIG. 1). In particular, the C-terminal region of GT198 is aligned with the third and the fourth BRC repeats of BRCA2. The demonstrated Rad51-binding activity among these three sequences provides functional support for the presence of a potential BRC repeat in GT198. The N-terminus of GT198 showed limited homology to the BRC repeats. The functional implication of their sequence homology is that GT198 could compete with BRCA2 in binding to Rad51 through the BRC repeat region as illustrated in Figure 1c.

Example 2

GT198 is Co-Expressed with BRCA1 and BRCA2

The endogenous nuclear expression pattern of GT198 is remarkably similar to or almost indistinguishable from both BRCA1 and BRCA2 expression in mice (Chodosh, L. A., *J Mammary Gland Biol Neoplasia*, 3:389-402 (1998)). GT198 protein expression increases in primitive ectoderm at four days of embryoid bodies derived from embryonic stem cells. Consistent with the previous Northern blot analysis (Ko, L., et al., *Mol Cell Biol*, 22:357-69 (2002)), in situ hybridization revealed a marked increase in GT198 mRNA expression in neural tubes from E8.5 to E10.5 (data not shown). The expression peaks at E12.5 in all three germ layers and is downregulated at E18.5. In adult rodents, GT198 protein was predominantly found in testis with restricted expression in thymus, spleen and ovary by Western blot analysis (Ko, L., et al, *Mol Cell Biol*, 22:357-69 (2002)). Similar to BRCA1, GT198 mRNA expression can also be detected in different tissues. At the cellular level, GT198 protein expresses in spermatocytes of the testis and oocytes of the ovary, consistent with its essential function in testis and ovary since both male and female GT198 knockout mice are sterile (Petukhova, G. V., et al., *Dev Cell*, 5:927-36 (2003)). In ovary, GT198 has high levels of nuclear expression in granulosa cells of the secondary and Graafian follicles but not in the primordial follicles or the corpus luteum. Theca cells have low levels of nuclear expression. This pattern is potentially associated with cycled steroid hormone action given that GT198 interacts with steroid receptors and stimulates receptor-mediated gene regulation (Ko, L., et al, *Mol Cell Biol*, 22:357-69 (2002)). The remarkably similar patterns among GT198, BRCA1 and BRCA2 expression (Lane, T. F., et al., *Genes Dev*, 9:2712-22 (1995); Sharan, S. K. & Bradley, A., *Genomics*, 40:234-41 (1997); Durocher, F., et al., *J Histochem Cytochem*, 45:1173-88 (1997); Blackshear, P. E., et al., *Oncogene*, 16:61-8 (1998)), suggest that they may have a close functional relationship in same developmental pathways.

Example 3

Alternatively Spliced GT198 Variants Inhibit Wild Type GT198

Figure 2A:
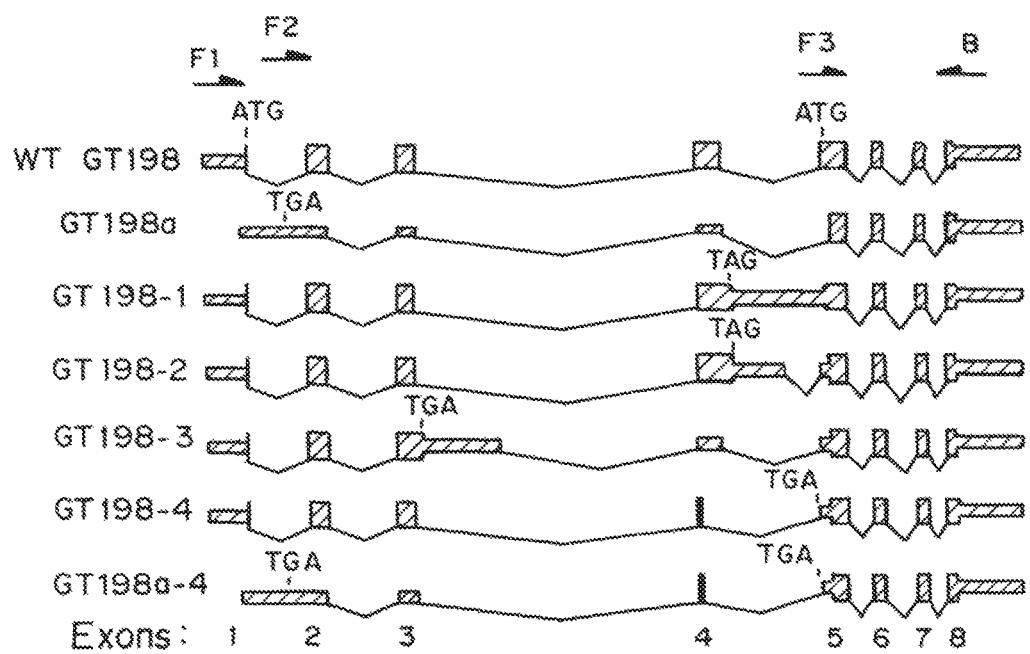
FIG. 2a is a schematic representation of the human GT198 variants identified by rapid amplification of 5' complementary DNA ends (5' RACE) and sequencing (not to scale). Mammalian GT198 has 8 exons. Introns are shown as lines, exons as bars, protein coding regions as thick bars. Deduced translation start and stop codons are indicated. Primer positions are shown at the top.

During RT-PCR analysis of human GT198 mRNA expression, a number of GT198 alternative splice variants were identified. Alternative splicing of GT198 is tissue-specific with more variety of splicing variants were found in embryonic tissues or in cancer cells than in normal adult tissues. Sequencing results showed that all alternative splicing events occur strictly at the GT-AG consensus sites, some of which are supported by NCBI EST evidence. Interestingly, variations of alternative splicing always occurred at the 5' half of the gene, and all generate premature stop codons with early termination of translation (FIG. 2a). All variant transcripts contain an open reading frame encoding the DBD (aa 126-217) with BRC repeat homology. A few variants also encode the N terminus. These truncated forms of potential proteins are devoid of the leucine zipper at amino acids 89-117 (Ko, L., et al., *Mol Cell Biol*, 22:357-69 (2002)), and thus would not form a dimer similar to the wild type. In addition, two alternative transcriptional start sites differing by the 5' at the first exon have been identified by 5'RACE. The longer transcripts at 5' end encode the wild type as well as the variants designated as GT198 1-4. The shorter transcripts at 5' end always retain the first intron and encode variants designated as GT198a and GT198a-4. The dual transcriptional start sites, present in both human and mouse, suggest the differential usage of promoters by wild type and variants. Of note, human BRCA1 is also known to have dual transcriptional start sites (hodosh, L. A., *J Mammary Gland Biol Neoplasia*, 3:389-402 (1998)) although their linkage to each variant was uncharacterized due to its large gene size.

Figure 2B:
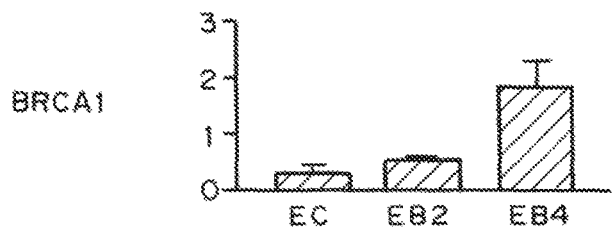
FIGS. 2b-e are a bar graphs of relative mRNA levels in undifferentiated P19 stem cells (EC) induced with 500 nM retinoic acid (RA) up to 4 days to form embryoid bodies (EB2-EB4). Relative mRNA levels of BRCA1 (FIG. 2b), BRCA1delta11b (FIG. 2c), GT198 (FIG. 2d), or GT198a (FIG. 2e) were obtained using real-time polymerase chain reaction. Results are shown as means+s.e.m. of relative mRNA level.
Figure 2C:
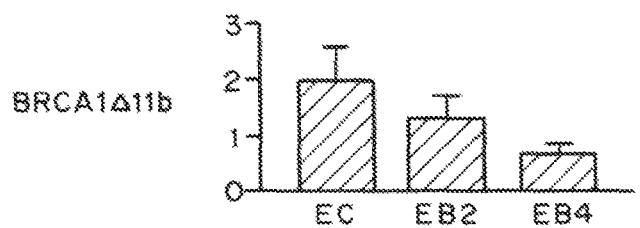
Figure 2D:
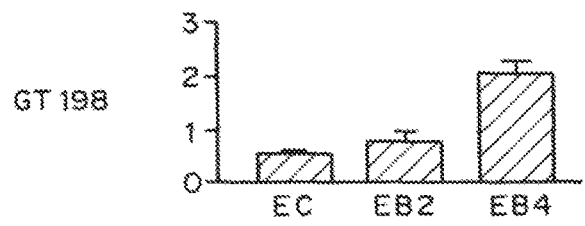
Figure 2E:
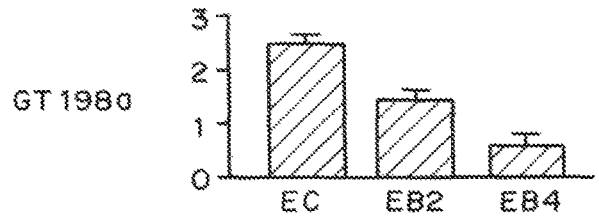
Figure 3A:
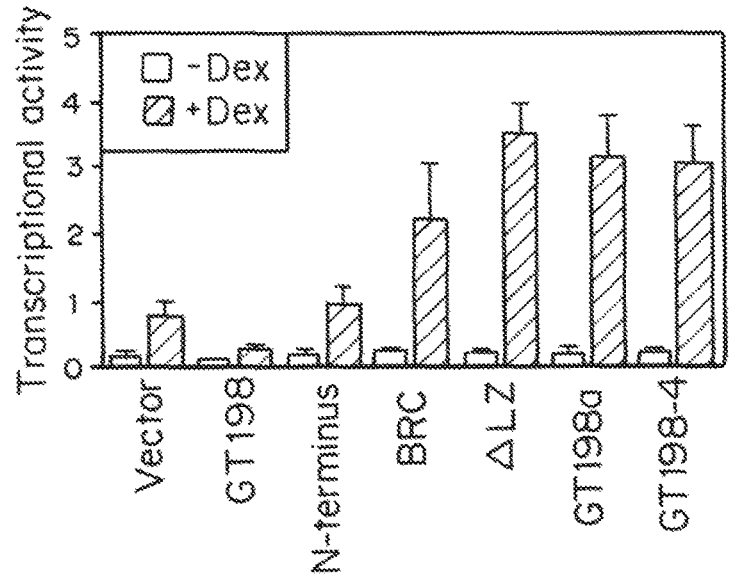
FIG. 3a is a bar graph of transcriptional activity in P19 cells transiently transfected with the indicated together with an MMTV-luciferase reporter (100 ng) and a glucocorticoid receptor (10 ng) that binds to the MMTV promoter. Cells were induced in the presence (solid bars) or the absence (clear bars) of ligand dexamethasone (100 nM) overnight and the luciferase activity was measured by a Dynex luminometer.
Figure 3B:
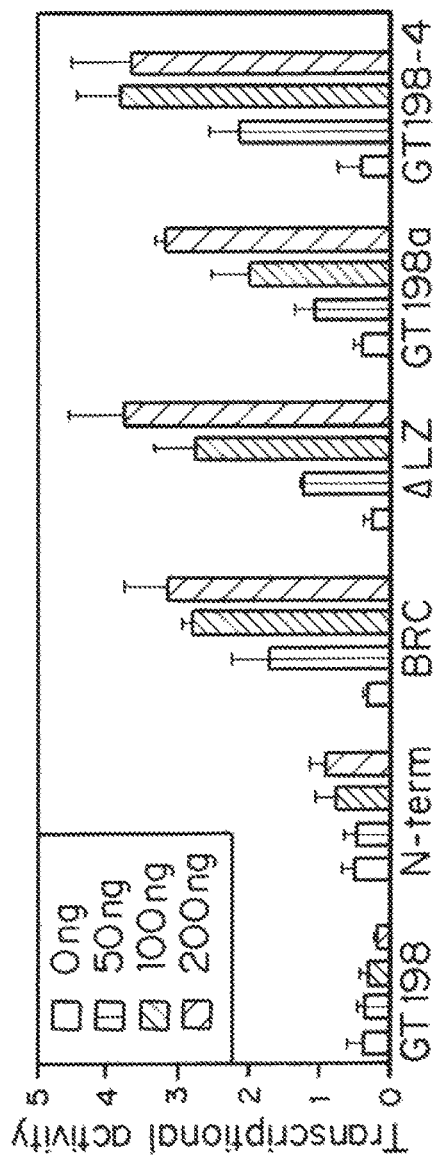
FIG. 3b is a bar graph of transcriptional activity of P19 cells transfected as in FIG. 3a except using an increasing amount of plasmids—0.0 ng (clear bars), 50 ng (shaded bars), 100 ng (hatched bars), and 200 ng (solid bars) and induced by dexamethasone (100 nM). Luciferase activities shown are means of triplicate transfections+s.e.m. (n=3).

The functional importance of GT198 alternative splicing in a stem cell differentiation system was then investigated. Variant GT198a with the retention of intron 1 was identified as a predominant variant form in stem cells of both human and mouse. During retinoic acid-induced mouse P19 stem cell differentiation, a marked decrease in GT198a and an increase in wild type GT198 mRNA were detected by RT-PCR and verified by quantification (FIGS. 2d-e). Interestingly, we found that BRCA1 and its variant BRCA1delta11b had a similar switched expression pattern as to GT198 and GT198a (FIGS. 2b-c), which is consistent with a previously reported Northern blot analysis of BRCA1 in mouse embryos (Hakem, R. et al., Cell, 85:1009-23 (1996)). The data imply that dual promoters in both genes are differentially regulated during embryoid body formation. GT198a mRNA is more abundant than GT198 mRNA inferred by using common primers that detect both. At the protein level, however, neither GT198a nor GT198-4 variants produces sufficient amount of variant proteins when detected by Western blot using GT198 protein fragments as controls. Even when abundant variant mRNA was present, only a trace amount of variant protein corresponding to GT198 DBD with BRC repeat homology can be detected only by immunoprecipitation when overexpressed in 293 cells or by immunofluorescent staining possibly due to the apoptosis of transfected cells. Therefore, the nuclear protein detected by immunohistochemical staining in normal tissues should be mainly wild type GT198 protein. Surprisingly, when transcriptional activity was tested in P19 stem cells using a mouse mammary tumor virus (MMTV) promoter-luciferase reporter system, variants GT198a and GT198-4 showed robust stimulation of transcription, while wild type GT198 repressed the transcriptional activity of MMTV promoter (FIG. 3a-b). The DBD with BRC repeat homology and a leucine zipper deletion mutant that prevented GT198 dimerization also showed transcriptional activation. The N terminus did to have significant activity. Consistent with the report that the DBD is required for GT198 activity (Enomoto, R. et al., J Biol Chem, 279:35263-72 (2004)), the data suggest that the GT198 DBD with BRC repeat homology, which was encoded by all variant mRNA, may compete with wild type GT198 and counteract its activity. Although detailed mechanisms need to be further elucidated, it is possible that the GT198 splice variants may serve as natural dominant negatives. In addition to the competition at protein level, the variants could prevent wild type mRNA expression through competitive alternative splicing or through yet-to-be-identified downstream RNA interference.

Importantly, similar regulation may exist for BRCA1 or BRCA2 if their inhibitory variants can be thoroughly studied. Nonetheless, through potential multiple mechanisms, alternatively spliced variants of GT198 inhibit the wild type.

Example 4

Overexpression of GT198 Splice Variants Block Rad51 foci Formation, Induce Apoptosis and Promote Cytoplasmic Translocation of Wild Type GT198

GT198 variants were tested for their effect on Rad51 foci formation upon ionizing radiation. HeLa cells were cotransfected with GFP-tagged Rad51 and with Flag-tagged constructs encoding GT198, variants GT198a, GT198-4, the N-terminal domain, the DBD with BRC repeat homology, or the leucine zipper deletion mutant. Cells were—irradiated to induce Rad51 foci before analyzed by immunofluorescent staining. As compared to the untransfected control, neither GT198 nor the N-terminus disrupted the Rad51 foci, while all DBD-encoding proteins with BRC repeat homology, including the two GT198 variants, blocked the foci formation. The foci disruption caused a homogenous expression of Rad51 not only in the nucleus, but also diffusing into the cytoplasm. Interestingly, while wild type GT198 is exclusively nuclear, all its fragments, mutants, or variants had cytoplasmic expression. Dimerization may be important for their subcellular localization and that the GT198 dimer is involved in Rad51-associated function (Pezza, R. J., et al., Genes Dev, 21:1758-66 (2007)). Detailed examination of a large number of transfected cells showed that cells with disrupted Rad51 foci also have altered morphology with shrinking nuclei. TUNEL assays confirmed that the DBD-containing monomeric proteins including splice variants induced marked apoptosis with DNA fragmentation, implicating that wild type GT198 is essential for the cell survival in culture. The N terminus showed cytoplasmic expression without induction of apoptosis or disruption of Rad51 foci, possibly because the essential functional unit of GT198 requires its DBD with BRC repeat homology. These data suggest that the BRC repeat region that competes or blocks GT198 normal activity. The loss of the wild type function triggers apoptosis. This conclusion is consistent with the transcriptional studies described above and also with the reported DNA-binding activity in which the DBD of GT198 is required (Enomoto, R. et al., J Biol Chem, 279:35263-72 (2004)). Variant overexpression was examined to determine if it influenced endogenous wild type GT198 expression by using non-overlapping antibodies against either the N or the C terminus. The results revealed a punctuated pattern of endogenous GT198 that changes levels through the cell cycle. BRCA1 expression is also known to be regulated during cell cycle. When an antibody against the N terminus of GT198 is analyzed with the C-terminal tagged variants, endogenous GT198 became cytoplasmic under the induction of variant activity. Cytoplasmic expression was also observed using an antibody against the C terminus of GT198. In summary, overexpression of GT198 variants promotes wild type GT198 cytoplasmic translocation, impairs Rad51 foci formation and induces apoptosis.

Example 5

Overexpression of GT198 Variants in Human Breast and Ovarian Cancers and Mouse Tumor Models BRCA1 is a tumor suppressor, and its functional loss predisposes to breast and ovarian cancers. Cytoplasmic BRCA1 overexpression in breast cancers has been previously reported in a high percentage of cases (Al-Mulla, F., et al., J Histochem Cytochem, 53:621-9 (2005)), indicating the connection between increased variants and wild-type deficiency. Indeed, many identified mutations of BRCA1 alter its splicing. This prompted immunohistochemistry analyses of GT198 expression in primary breast and ovarian cancers. Using the antibody against full-length GT198, 238 cases of ovarian cancer and 114 cases of breast cancers were screened with normal controls in tissue arrays. In ovarian cancer cases, cytoplasmic expression of GT198 was found in 13.4% of stromal cells and in 29.8% of epithelial cells (Table 1). Normal human adult ovaries are devoid of cytoplasmic GT198 staining suggesting the cytoplasmic expression is associated with cancers. Most of the ovarian cancer cases except benign fibromas and fibrothecomas did not show nuclear staining of GT198 (not shown). A characteristic high level of cytoplasmic expression in exclusive stromal cells was found in most of epithelial subtypes of ovarian cancers, including serous, mucinous, endometrial, clear cell carcinomas, and also in granulosa-theca cell carcinoma. GT198 variant mRNA can also be detected in ovarian cancers and the cytoplasmic protein can be recognized by antibodies against both the N- and C-terminus of GT198, suggesting that either variant expression or wild type cytoplasmic translocation are present in tumors. In one case at early stage, the GT198 positive cells are located in theca cell areas surrounding the follicles while the follicles continued to elongate and disintegrate into cord structures. When a large number of cases were examined, it appears that at later stages of cancer development, accumulated granulosa cells underwent an epithelial transition to evolve into epithelial types. GT198 positive cells are most frequently found underlining the epithelium and at later stages they squeeze into channels of stromal areas when tumor mass becomes significant. The GT198 positive cells are absent in metastatic tumors that originate from other sites suggesting the involvement of GT198 in ovarian cancer development (Table 1). It is unknown whether these GT198 positive stromal cells were related to theca cells. However, their distribution patterns in developing cancer tissues imply that these positive cells from each epithelial subtype might have the same origin. Supporting to the findings, considerable evidence has previously demonstrated that ovarian surface epithelium also known as germinal epithelium shares the same origin as follicles, and that oogenesis occurs in ovarian surface epithelium (Nishida, T. & Nishida, N., *Reprod Biol Endocrinol*, 4:42 (2006); Bukovsky, A., et al., *Endocrine*, 26:301-16 (2005)). The observation using GT198 as a marker is consistent with the evidence that hormone-responsive granulosa and theca cells may evolve into epithelial types of ovarian cancers.

In the analysis of 114 cases of human breast cancers, cytoplasmic GT198 expression was found in 17.5% of stromal cells and in 48.2% of epithelial or myoepithelial cells (Table 1). Normal breast tissue is negative for GT198 expression with the exception of a few positive stroma cells. Myoepithelial expression of cytoplasmic GT198 is frequently found with hyperplasia or with disrupted ductal structure. Since GT198 regulates hormone-stimulated nuclear receptor signaling, its alteration in myoepithelial cells supports the existing evidence that the hormone-responsive myoepithelial layer (Strum, J. M., *Cell Tissue Res*, 193:155-61 (1978)), plays a critical role in breast cancer development (Gudjonsson, T., et al., *J Mammary Gland Biol Neoplasia*, 10:261-72 (2005)). Furthermore, in mouse tumor models carrying MMTV-Ras or the polyomavirus middle T antigen transgenes, GT198 has massive cytoplasmic expression in the stroma of mammary gland tumors, as compared to the nontransgenic normal tissue, even before morphological hyperplasia occurs. This data indicates that viral oncogene activation induces GT198 variant overexpression. Since GT198 variants stimulate the MMTV promoter (FIG. 3a-b), positive feedback between oncogene Ras and GT198 variant expression may facilitate tumor initiation. A cytoplasmic to nuclear GT198 transition occurs only at later stages when transformed tumor cells accumulate.

In summary, breast and ovarian cancers contain GT198 positive cells with cytoplasmic expression. The increased GT198 variant activity potentially causes wild type functional deficiency and disrupts differentiation of cells that are survived from apoptosis. To further confirm this notion, nude mouse mammary glands were injected with mouse P19 stem cells stably transfected with either wild type GT198 or variant GT198a. The data suggested that variant GT198a but not wild type GT198 transfected cells induced significant tumor growth. The collective evidence in human ovarian and breast cancers and mouse tumor models suggests that GT198 variant overexpression is an early event during tumor development, which reflects the functional connection between GT198 and BRCA1.

TABLE 1

Cytoplasmic Expression of GT198 in Human Breast and Ovarian Cancers

| | Total n | Stromal expression n (%) | Epithelial expression n (%) |
|---|---|---|---|
| Ovarian cancer subtype | | | |
| Serous | 112 | 7 (6.3) | 45 (40.2) |
| Mucinous | 33 | 16 (48.5) | 14 (42.4) |
| Endometrioid | 11 | 3 (27.3) | 6 (54.5) |
| Clear cell | 15 | 1 (6.7) | 4 (26.7) |
| Brenner | 1 | 0 (0) | 0 (0) |
| Undifferentiated | 7 | 0 (0) | 0 (0) |
| Granulosa-theca | 12 | 5 (41.7) | 1 (8.3) |
| Sertoli-Ledig | 1 | 0 (0) | 0 (0) |
| Fibroma-thecoma | 14 | 0 (0) | 0 (0) |
| Dysgerminoma | 10 | 0 (0) | 0 (0) |
| Embryonal | 3 | 0 (0) | 1 (33.3) |
| Muellerian | 3 | 0 (0) | 0 (0) |
| Metastasis from distance | 16 | 0 (0) | 0 (0) |
| Normal | 14 | 0 (0) | 0 (0) |
| Total case of tumor | 238 | 32 (13.4%) | 71 (29.8%) |
| Breast cancer subtype | | | |
| Invasive ductal | 64 | 12 (18.7) | 34 (53.1) |
| Invasive lobular | 11 | 0 (0) | 4 (36.4) |
| Medullary | 4 | 0 (0) | 1 (25.0) |
| Carcinoma in situ | 6 | 2 (33.3) | 4 (66.7) |
| Hyperplasia | 9 | 1 (11.1) | 7 (77.8) |
| Fibroadenoma | 3 | 0 (0) | 0 (0) |
| Lymph node metastasis | 17 | 5 (29.4) | 5 (29.4) |
| Normal | 4 | 0 (0) | 0 (0) |
| Total case of tumor | 114 | 20 (17.5%) | 55 (48.2%) |

Example 6

Germline Mutations of GT198 in Early Onset Breast Cancer Patients

Figures 4B, 4C:
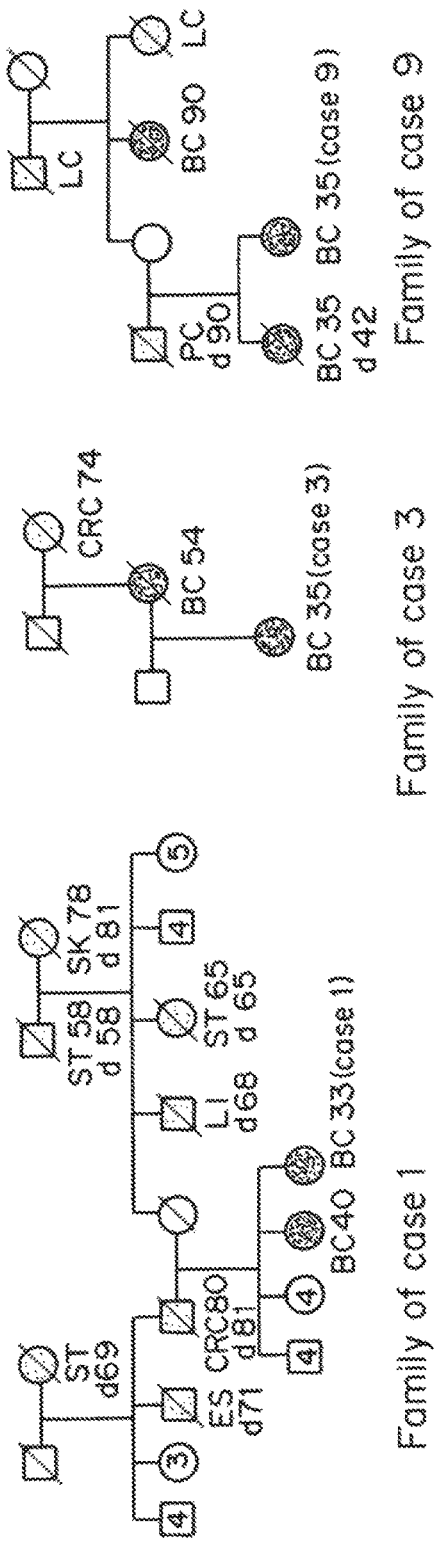
FIG. 4b is a table summarizing the year of onset, allelic mutations and SNPs (r52292751, rs2292752) identified.
FIG. 4c is a pedigree of the families of case 1, case 3, and case 9 with breast cancer (filled circles and squares), other types of cancer (shaded circles and squares), or healthy (clear circles and squares). Circles represent women and squares represent men. Numbers inside indicate additional healthy siblings. Slash symbols indicate deceased individuals. Cancer types, year of onset, and year of death (d) are shown as available (BC, breast cancer; CRC, colorectal cancer; ST, stomach cancer; SK, skin cancer; LI, liver cancer; ES, esophagus cancer; PC, prostate cancer; LC, lung cancer).

To seek genetic evidence for the involvement of GT198 in breast cancer, GT198 mutations in genomic DNA and RNA isolated from immortalized blood lymphocytes from nine early onset (<40 years) breast cancer cases whom were negative for BRCA1 and BRCA2 mutations. Southern blot, real-time PCR, genomic walking, RT-PCR, and sequence analyses were performed. Southern blot analysis showed the presence of abnormal bands in case 3 and case 9. Subsequent sequencing confirmed the allelic point mutations at restriction sites in these two cases. In case 3, the C to G mutation is at 31 bp after the stop codon in 3' UTR, c.*31C>G. In case 9, a C to T mutation in intron 4, 88 bp away from the splicing junction was identified, c.337+88C>T. Excluding the large intron 3, all exons and introns were sequenced in these nine cases. A mono-allelic C to T mutation (Q104Stop, c.310C>T) was identified in exon 4 of case 1. This nonsense mutation generates a premature stop codon and is predicted to prevent the translation of full length GT198 but permit the translation of the variant protein containing the BRC repeat homology encoded by exons 5-8. The impact of these sequence alterations on alternative splicing was evaluated by RT-PCR. The results indeed suggested the increased variant mRNA expression in immortalized lymphocytes in cases with mutations, although detailed mechanisms remain to be studied. GT198a variant is markedly increased in case 1 and case 3, and GT198-4 variant is increased in case 9. The variant cDNA of case 1 and case 3 were found to carry the same mutations. Real-time PCR analysis did not detect copy gain or loss of GT198 in these nine cases (not shown). In addition, two SNPs were found in intron 4 during the sequencing analysis (FIG. 4b). Based on the HapMap database at NCBI, these two SNPs are common SNPs and are unlikely to be strong susceptibility alleles. The GT198 gene covers two haploblocks joined at its large intron 3 containing multiple Alu and L2 repeats (FIG. 4a), however, we have not detected any rearrangement in these nine cases by real-time PCR and genomic walking analyses. More unidentified mutations could exist to affect alternative splicing since the promoter/enhancer regions have not been analyzed. The family history of cases carrying mutations was further examined and it was found that multiple individuals in each family have cancers including breast cancer in a first degree relative (FIG. 4c). The case 1 sister had breast cancer at the age of 40 and DNA was available at the time of this report. Sequence analysis showed that she also carried the same c.310C>T (Q104Stop) mutation. These data collectively indicate the presence of germline mutations of GT198 that promote GT198 variant expression in early onset breast cancers.

```
SEQUENCE DATA
Underline is start and stop codons. Bold is the extra sequence invariants.
GT198 wt
                                                          (SEQ ID NO: 5)
cttcccatcagccaatcaccgttcgaggcccgccccgtcgccggaaggagccgtcgccccgagcaactacaa
cgtccggattctgagttgggtggcgggaaaggcatgagtaaaggccgggcagaagagcggcgggagccg
ccgggatcctcctgaggtacctgcaggagcagaaccggccctacagacccaggatgtgttcgggaacctacag
cgggaacacggactgggcaaggcggtggtggtgaagacgctggagcagctggcgcaacaaggcaagatcaa
agagaagatgtacggcaagcagaagatctattttgcggatcaggaccagtttgacatggtgagtgatgctgac
cttcaagtcctagatggcaaaatcgtggccctcactgctaaggtgcagagcttgcagcagagagccgctacat
ggaggctgagctcaaggaattatctagtgccctgaccacaccagagatgcagaaagaaatccaggagttaaag
aaggaatgcgctggctacagagagagattgaagaacattaaagcagctaccaatcatgtgactccagaagaga
aagagcaggtgtacagagagaggcagaagtactgtaaggagtggaggaagaggaagaggatggctacagagct
gtctgatgcaatacttgaaggatacccaagagcaagaagcagttattgaggaagtttgggatagagacggatg
aagattacaacgtcacactcccagaccccgaggggcc Protein:
                                                          (SEQ ID NO: 6)
MSKGRAEAAAGAAGILLRYLQEQNRPYSSQDVFGNLQREHGLGKAVV
VKTLEQLAQQGKIKEKMYGKQKIYFADQDQFDMVSDADLQVLDGKIV
ALTAKVQSLQQSCRYMEAELKELSSALTTPEMQKEIQELKKECAGYRER
LKNIKAATNHVTPEEKEQVYRERQKYCKEWRKRKRMATELSDAILEGY
PKSKKQFFEEVGIETDEDYNVTLPDP GT198-1 isoform1
                                                          (SEQ ID NO: 7)
cttcccatcagccaatcaccgttcgaggcccgccccgtcgccggaaggagccgtcgccccgagcaactacaa
cgtccggattctgagttgggtggcgggaaaggcatgagtaaaggccgggcagaagagcggcgggagccg
ccgggatcctcctgaggtacctgcaggagcagaaccggccctacagacccaggatgtgttcgggaacctacag
cgggaacacggactgggcaaggcggtggtggtgaagacgctggagcagctggcgcaacaaggcaagatcaa
agagaagatgtacggcaagcagaagatctattttgcggatcaggaccagtttgacatggtgagtgatgctga
ccttcaagtcctagatggcaaaatcgtggccctcactgctaaggtgcagagcttgcagcagagctgccgctac
atggaggctggtaggactgggtagccctccaaagtgcccataggcttaggttcattctagaggtcaggaatt
actaaatgaatggttcaatgactgcagcatcttgttgcagctaagacccctttgagggctcccttaggcataa
aaagaaatgtaggataactaacggctttigtgtaccaacaaatggacaagatacgcatttgttctccctgcca
cgattatcagtacactgtccccacgtttccctttattcctgcttctttaactggctacgcctaagtaagtgtt
caacctcacacccacgccacttgtagatggaggaagaaagaaaattagaagaataaataatcctgtatggctt
agtttccatgtgagatgatagatccagagcaaggtggaacacctcagggagcacccactgggaaagacagaac
tccttcctcaggggtagcaagtgacccaggggatgtggtticagagctcaaggaattatctagtgccctga
ccacaccagagatgcagaaagaaatccaggagttaaagaaggaatgcgctggctacagagagagattgaagaa
cattaaagcagctaccaatcatgtgactccagaagagaaagagcaggtgtacagagagaggcagaagtactgt
aaggagtggaggaagaggaagaggatggctacagagctgtctgatgcaatacttgaaggatacccaagagca
agaagcagttattgaggaagtttgggatagagacggatgaagattacaacgtcacactcccagacccctgaggg
gcc GT198-2 isoform2
                                                          (SEQ ID NO: 8)
Cttcccatcagccaatcaccgttcgaggcccgccccgtcgccggaaggagccgtcgccccgagcaactacaa
cgtccggattctgagttgggtggcgggaaaggcatgagtaaaggccgggcagaagctggcgggagccg
ccgggatcctcctgaggtacctgcaggagcagaaccggccctacagctcccaggatgtgttcgggaacctacag
cgggaacacggactgggcaaggcggtggtggtgaagacgctggagcagctggcgcaacaaggcaagatcaa
agagaagtgtacggcaagcagaagatctattttgcggatcaggaccagtttgacatggtgagtgatgctga
ccttcaagtcctagatggcaaaatcgtggccctcactgctaaggtgcagagcttgcagcagagctgccgctaca
tggaggctggtaggactgggtagccctccaaagtgcccataggcttaggttcattctagaggtcaggaattac
taaatgaatggttcaatgactgcagcatcttgttgcagctaagacccctttgagggctcccttaggcataaaa
agaaatgtaggataactaacggctttigtgtaccaacaaatggacaagatacgcatttgttctccctgccacg
attatcagtacactgtccccacgtttccctttattcctgcttctttaactggctacgcctaagtaagtagctca
aggaattatctagtgccctgaccacaccagagatgcagaaagaaatccaggagttaaagaaggaatgcgctggc
tacagagagagattgaagaacattaaagcagctaccaatcatgtgactccagaagagaaagagcaggtgtacag
agagaggcagaagtactgtaaggagtggaggaagaggaagaggatggctacagagctgtctgatgcaatacttg
aaggatacccaagagcaagaagcagttattgaggaagtttgggatagagacggatgaagattacaacgtcacac
tcccagaccccgaggggcc
```

-continued

GT198-3 isoform3

(SEQ ID NO: 9)

Cttcccatcagccaatcaccgttcgaggcccgcccccgtcgccggaaggagccgtcgccccgagcaactacaa
cgtccggattctgagtttgggtggcgggaaaggc<u>gat</u>gagtaaaggccgggcagaagctggcggggagccg
ccgggatcctcctgaggtacctgcaggagcagaaccggccctacagctcccaggatgtgttcgggaacctacag
cgggaacacggactgggcaaggcggtggtggtgaagacgctggagcagctggcgcaacaaggcaagatcaa
agagaagatgtacggcaagcagaagatctattttggatcag**tgaggagaacttgcgccgattgtcacccat
gagagcccgacaacgggtgaatctactcctggtgtgaactctttggggacaaggcccccatggaaaactc
acctgtcttaggccaccatccttaaatcaag**gaccagtttgacatggtgagtgatgctgaccttcaagtcc
tagatggcaaaatcgtggccctcactgctaaggtgcagagcttgcagcagagctgccgctacatggaggctgag
ctcaaggaattatctagtgccctgaccacaccagagatgcagaaagaaatccaggagttaaagaaggaatgcgc
tggctacagagagagattgaagaacattaaagcagctaccaatcatgtgactccagaagagaaagagcaggtgt
acagagagaggcagaagtactgtaaggagtggaggaagaggaagaggatggctacagagctgtctgatgcaata
cttgaaggatacccaagagcaagaagcagttctttgaggaagtttgggatagagacggatgaagattacaacgt
cacactcccagacccct<u>tga</u>ggggcc GT198-4 isoform4

(SEQ ID NO: 10)

cttcccttcagccaatcaccgttcgaggcccgcccccgtcgccggaaggagccgtcgccccgagcaactacaa
cgtccggctttctgagtttgggtggcgggaaaggc<u>gat</u>gagtaaaggccgggcagaagctgcggcgggagccg
ccgggatcctcctgaggtacctgcaggagcagaaccggccctacagctcccaggatgtgttcgggaacctacag
cgggaacacggactgggcaaggcggtggtggtgaagacgctggagcagctggcgcaacaaggcaagatcaa
agagaagatgtacggcaagcagaagatctattttgcggatcaggaccagtttgacatgagctcaaggaatta
tctagtgccctgaccacaccagagatgcagaaagaaatccaggagttaaagaaggaatgcgctggctacagag
agagattgaagaacattaaagcagctaccaatcatgtgactccagaagagaaagagcaggtgtacagagagaggc
agaagtactgtaaggagtggaggaagaggaagaggatggctacagagctgtctgatgcaatacttgaaggatacc
caagagcaagaagcagttctttgaggaagtttgggatagagacggatgaagattacaacgtcacactcccagacc
cct<u>tga</u>ggggcc hGT198a 761 bp (SEQ ID NO: 11)

gggaaaggc<u>gat</u>gagtaaaggccgggcagaagagcggcgggag**gtaacggcgccgtgggcgcggggaa
gacccgggagggcagtgggtgaggaggtcggttgagtggccccctcccctgcctttctctccgtag**ccgccg
ggatcctcctgaggtacctgcaggagcagaaccggccctacagctcccaggatgtgttcgggaacctacagcgg
gaacacggactgggcaaggcggtggtggtgaagacgctggagcagctggcgcaacaaggcaagatcaaaga
gaagatgtacggcaagcagaagatctattttgcggatcaggaccagtttgacatggtgagtgatgctgacct
tcaagtcctagatggcaaaatcgtggccctcactgctaaggtgcagagcttgcagcagagctgccgctacatgga
ggctgagctcaaggaattatctagtgccctgaccacaccagagatgcagaaagaaatccaggagttaaagaagga
atgcgctggctacagagagagattgaagaacattaaagcagctaccaatcatgtgactccagaagagaaagagca
ggtgtacagagagaggcagaagtactgtaaggagtggaggaagaggaagaggatggctacagagctgtctgatgc
aatacttgaaggatacccaagagcaagaagcagttctttgaggaagtttgggatagagacggatgaagattacaa
cgtcacactcccagacccct<u>tga</u>ggggcc hGT198a-4 664 bp (SEQ ID NO: 12)

gggaaaggc<u>gat</u>gagtaaaggccgggcagaagagcggcgggag**gtaacggcgccgtgggcgcggggaa
gacccgggagggcagtgggtgaggaggtcggttgagtggccccctcccctgccttctctccgtag**ccgccg
ggatcctcctgaggtacctgcaggagcagaaccggccctacagctcccaggatgtgttcgggaacctacagcgg
gaacacggactgggcaaggcggtggtggtgaagacgctggagcagctggcgcaacaaggcaagatcaaaga
gaagatgtacggcaagcagaagatctattttgcggatcaggaccagtttgacatgagctcaaggaattatctag
tgccctgaccacaccagagatgcagaaagaaatccaggagttaaagaaggaatgcgctggctacagagagagat
tgaagaacattaaagcagctaccaatcatgtgactccagaagagaaagagcaggtgtacagagagaggcagaag
tactgtaaggagtggaggaagaggaagaggatggctacagagctgtctgatgcaatacttgaaggatacccaa
gagcaagaagcagttctttgaggaagtttgggatagagacggatgaagattacaacgtcacactcccagacccc
<u>tga</u>ggggcc All variant encode a C-terminal protein: 92 aa (SEQ ID NO: 13)

MQKEIQELKKECAGYRERLKNIKAATNHVTPEEKEQVYRERQKYCKEW
RKRKRMATELSDAILEGYPKSKKQFFEEVGIETDEDYNVTLPDP

---

I claim:

1. A method for identifying a chemical compound as a potential anticancer drug for the treatment of human cancer, the method comprising:
   a) screening a chemical compound to determine whether the chemical compound binds to GT198 protein consisting of SEQ ID NO:6 or SEQ. ID NO:13;
   b) measuring the ability of the chemical compound to inhibit transcriptional activity mediated by GT198 protein consisting of SEQ ID NO:6 or SEQ. ID NO:13; and
   c) identifying a chemical compound that both binds GT198 protein consisting of SEQ. ID NO:6 or SEQ ID NO:13 and inhibits transcriptional activity mediated by GT198 protein consisting of SEQ ID NO:6 or SEQ NO:13 as a potential anticancer drug for the treatment of human cancer.

2. The method of claim 1, wherein the chemical compound is natural or synthetic.

3. The method of claim 1, wherein the chemical compound comprises a combination of chemical ingredients.

* * * * *

SEQUENCE LISTING

<160> NUMBER OF SEQ ID NOS: 13

<210> SEQ ID NO 1
<211> LENGTH: 46
<212> TYPE: PRT
<213> ORGANISM: Homo sapiens

<400> SEQUENCE: 1

Asn Ile Lys Asp Phe Glu Thr Ser Asp Thr Phe Phe Gln Thr Ala Ser
1               5                   10                  15

Gly Lys Asn Ile Ser Val Ala Lys Glu Ser Phe Asn Lys Ile Val Asn

```
                  20                  25                  30

Phe Phe Asp Gln Lys Pro Glu Glu Leu His Asn Phe Ser Leu
         35                  40                  45

<210> SEQ ID NO 2
<211> LENGTH: 46
<212> TYPE: PRT
<213> ORGANISM: Homo sapiens

<400> SEQUENCE: 2

Asp Glu Lys Ile Lys Glu Pro Thr Leu Ile Gly Phe His Thr Ala Ser
1               5                  10                  15

Gly Lys Lys Val Lys Ile Ala Lys Glu Ser Leu Gly Lys Val Lys Asn
             20                  25                  30

Leu Phe Asp Glu Lys Glu Gln Gly Thr Ser Glu Ile Thr Ser
         35                  40                  45

<210> SEQ ID NO 3
<211> LENGTH: 46
<212> TYPE: PRT
<213> ORGANISM: Homo sapiens

<400> SEQUENCE: 3

Glu Cys Ala Gly Tyr Arg Glu Arg Leu Lys Asn Ile Lys Ala Ala Thr
1               5                  10                  15

Asn His Val Thr Pro Glu Glu Lys Glu Gln Val Tyr Arg Glu Arg Gln
             20                  25                  30

Lys Tyr Cys Lys Glu Trp Arg Lys Arg Lys Met Ala Thr
         35                  40                  45

<210> SEQ ID NO 4
<211> LENGTH: 91
<212> TYPE: DNA
<213> ORGANISM: Artificial Sequence
<220> FEATURE:
<223> OTHER INFORMATION: Synthetic SiRNA

<400> SEQUENCE: 4
gtaacggcgc cgtgggcgcg gggaagaccc gggagggcag tgggtgagga ggtcggttga      60
gtggccccct cccctgcctt tctctccgta g                                    91

<210> SEQ ID NO 5
<211> LENGTH: 769
<212> TYPE: DNA
<213> ORGANISM: Homo sapiens

<400> SEQUENCE: 5
cttccccttc agccaatcac cgttcgaggc ccgcccccgt cgccggaagg agccgtcgcc      60
ccgagcaact acaacgtccg gctttctgag ttgggtggcg ggaaaggcga tgagtaaagg     120
ccgggcagaa gctgcggcgg gagccgccgg gatcctcctg aggtacctgc aggagcagaa     180
ccggccctac agctcccagg atgtgttcgg gaacctacag cgggaacacg gactgggcaa     240
ggcggtggtg gtgaagacgc tggagcagct ggcgcaacaa ggcaagatca aagaagaagat    300 gtacggcaag cagaagatct attttgcgga tcaggaccag tttgacatgg tgagtgatgc     360
tgaccttcaa gtcctagatg caaaatcgt ggccctcact gctaaggtgc agagcttgca     420
gcagagctgc cgctacatgg aggctgagct caaggaatta tctagtgccc tgaccacacc     480
agagatgcag aaagaaatcc aggagttaaa gaaggaatgc gctggctaca gagagagatt     540
```

```
gaagaacatt aaagcagcta ccaatcatgt gactccagaa gagaaagagc aggtgtacag    600
agagaggcag aagtactgta aggagtggag gaagaggaag aggatggcta cagagctgtc    660
tgatgcaata cttgaaggat accccaagag caagaagcag ttctttgagg aagttgggat    720
agagacggat gaagattaca acgtcacact cccagacccc tgaggggcc               769
```

<210> SEQ ID NO 6
<211> LENGTH: 217
<212> TYPE: PRT
<213> ORGANISM: Homo sapiens

<400> SEQUENCE: 6

```
Met Ser Lys Gly Arg Ala Glu Ala Ala Gly Ala Ala Gly Ile Leu
1               5                   10                  15

Leu Arg Tyr Leu Gln Glu Gln Asn Arg Pro Tyr Ser Ser Gln Asp Val
            20                  25                  30

Phe Gly Asn Leu Gln Arg Glu His Gly Leu Gly Lys Ala Val Val Val
        35                  40                  45

Lys Thr Leu Glu Gln Leu Ala Gln Gln Gly Lys Ile Lys Glu Lys Met
    50                  55                  60

Tyr Gly Lys Gln Lys Ile Tyr Phe Ala Asp Gln Asp Gln Phe Asp Met
65                  70                  75                  80

Val Ser Asp Ala Asp Leu Gln Val Leu Asp Gly Lys Ile Val Ala Leu
                85                  90                  95

Thr Ala Lys Val Gln Ser Leu Gln Gln Ser Cys Arg Tyr Met Glu Ala
            100                 105                 110

Glu Leu Lys Glu Leu Ser Ser Ala Leu Thr Thr Pro Glu Met Gln Lys
        115                 120                 125

Glu Ile Gln Glu Leu Lys Lys Glu Cys Ala Gly Tyr Arg Glu Arg Leu
    130                 135                 140

Lys Asn Ile Lys Ala Ala Thr Asn His Val Thr Pro Glu Glu Lys Glu
145                 150                 155                 160

Gln Val Tyr Arg Glu Arg Gln Lys Tyr Cys Lys Glu Trp Arg Lys Arg
                165                 170                 175

Lys Arg Met Ala Thr Glu Leu Ser Asp Ala Ile Leu Glu Gly Tyr Pro
            180                 185                 190

Lys Ser Lys Lys Gln Phe Phe Glu Glu Val Gly Ile Glu Thr Asp Glu
        195                 200                 205

Asp Tyr Asn Val Thr Leu Pro Asp Pro
    210                 215
```

<210> SEQ ID NO 7
<211> LENGTH: 1244
<212> TYPE: DNA
<213> ORGANISM: Homo sapiens

<400> SEQUENCE: 7

```
cttccccttc agccaatcac cgttcgaggc ccgccccgt cgccggaagg agccgtcgcc    60
ccgagcaact acaacgtccg gctttctgag ttgggtggcg ggaaaggcga tgagtaaagg   120
ccgggcagaa gctgcggcgg gagccgccgg gatcctcctg aggtacctgc aggagcagaa   180
ccggccctac agctcccagg atgtgttcgg gaacctacag cgggaacacg gactgggcaa   240
ggcggtggtg gtgaagacgc tggagcagct ggcgcaacaa ggcaagatca agagaagat   300 gtacggcaag cagaagatct attttgcgga tcaggaccga tttgacatgg tgagtgatgc   360
tgaccttcaa gtcctagatg gcaaaatcgt ggccctcact gctaaggtgc agagcttgca   420
```

```
gcagagctgc cgctacatgg aggctggtag gactgggtag cccctccaaa gtgcccatag      480
gcttaggttc attctagagg tcaggaatta ctaaatgaat ggttcaatga ctgcagcatc      540
ttgttgcagc taagacccct ttgctgggct cccttaggca taaaaagaaa tgtaggataa      600
ctaacggctt ttgtgtacca acaaatggac aagatacgca tttgttctcc ctgccacgat      660
tatcagtaca ctgtccccac gtttcccttt attcctgctt ctttaactgg ctacgcctaa      720
gtaagtgttc aacctcacac ccacgccact tgtagatgga ggaagaaaga aaattagaag      780
aataaataat cctgtatggc ttagtttcca tgtgagatga tagatccaga gcaaggtgga      840
acacctcagg gagcacccac tgggaaagac agaactcctt cctcagggt agcaagtgac       900 cccaggggga tgtggtttca gagctcaagg aattatctag tgccctgacc acaccagaga      960
tgcagaaaga aatccaggag ttaaagaagg aatgcgctgg ctacagagag agattgaaga     1020
acattaaagc agctaccaat catgtgactc agaagagaa agagcaggtg tacagagaga     1080
ggcagaagta ctgtaaggag tggaggaaga ggaagaggat ggctacagag ctgtctgatg     1140
caatacttga aggatacccc aagagcaaga agcagttctt tgaggaagtt gggatagaga     1200
cggatgaaga ttacaacgtc acactcccag accctgagg ggcc                      1244

<210> SEQ ID NO 8
<211> LENGTH: 1049
<212> TYPE: DNA
<213> ORGANISM: Homo sapiens

<400> SEQUENCE: 8 cttcccttc agccaatcac cgttcgaggc ccgcccccgt cgccggaagg agccgtcgcc       60
ccgagcaact acaacgtccg gctttctgag ttgggtggcg ggaaaggcga tgagtaaagg     120
ccgggcagaa gctgcggcgg gagccgccgg gatcctcctg aggtacctgc aggagcagaa     180
ccggccctac agctcccagg atgtgttcgg gaacctacag cgggaacacg gactgggcaa     240
ggcggtggtg gtgaagacgc tggagcagct ggcgcaacaa ggcaagatca agagaagat     300 gtacggcaag cagaagatct attttgcgga tcaggaccag tttgacatgg tgagtgatgc     360
tgaccttcaa gtcctagatg gcaaaatcgt ggccctcact gctaaggtgc agagcttgca     420
gcagagctgc cgctacatgg aggctggtag gactgggtag cccctccaaa gtgcccatag     480
gcttaggttc attctagagg tcaggaatta ctaaatgaat ggttcaatga ctgcagcatc     540
ttgttgcagc taagacccct ttgctgggct cccttaggca taaaaagaaa tgtaggataa     600
ctaacggctt ttgtgtacca acaaatggac aagatacgca tttgttctcc ctgccacgat     660
tatcagtaca ctgtccccac gtttcccttt attcctgctt ctttaactgg ctacgcctaa     720
gtaagtagct caaggaatta tctagtgccc tgaccacacc agagatgcag aaagaaatcc     780
aggagttaaa gaaggaatgc gctggctaca gagagagatt gaagaacatt aaagcagcta     840
ccaatcatgt gactccagaa gagaaagagc aggtgtacag agagaggcag aagtactgta     900
aggagtggag gaaggaag aggatggcta cagagctgtc tgatgcaata cttgaaggat      960
accccaagag caagaagcag ttctttgagg aagttgggat agagacggat gaagattaca    1020
acgtcacact cccagacccc tgaggggcc                                       1049

<210> SEQ ID NO 9
<211> LENGTH: 902
<212> TYPE: DNA
<213> ORGANISM: Homo sapiens
```

<400> SEQUENCE: 9

```
cttccccttc agccaatcac cgttcgaggc ccgcccccgt cgccggaagg agccgtcgcc    60
ccgagcaact acaacgtccg gctttctgag ttgggtggcg ggaaaggcga tgagtaaagg   120
ccgggcagaa gctgcggcgg gagccgccgg gatcctcctg aggtacctgc aggagcagaa   180
ccggccctac agctcccagg atgtgttcgg gaacctacag cgggaacacg gactgggcaa   240
ggcggtggtg gtgaagacgc tggagcagct ggcgcaacaa ggcaagatca agagaagat    300
gtacggcaag cagaagatct attttgcgga tcaggtgagg agaacttgcg ccgattgtca   360
cccatgagag cccgacaacg ggtgaatcta ctcctggtgt gaactctttg ggacaaggc    420
cccccatgga aaactcacct gtcttaggcc accatcctta aatcaaggac cagttttgaca  480
tggtgagtga tgctgacctt caagtcctag atggcaaaat cgtggccctc actgctaagg   540
tgcagagctt gcagcagagc tgccgctaca tggaggctga gctcaaggaa ttatctagtg   600
ccctgaccac accagagatg cagaaagaaa tccaggagtt aaagaaggaa tgcgctggct   660
acagagagag attgaagaac attaaagcag ctaccaatca tgtgactcca gaagagaaag   720
agcaggtgta cagagagagg cagaagtact gtaaggagtg gaggaagagg aagaggatgg   780
ctacagagct gtctgatgca atacttgaag ataccccaa gagcaagaag cagttctttg    840
aggaagttgg gatagagacg gatgaagatt acaacgtcac actcccagac ccctgagggg   900
cc                                                                  902
```

<210> SEQ ID NO 10
<211> LENGTH: 672
<212> TYPE: DNA
<213> ORGANISM: Homo sapiens

<400> SEQUENCE: 10

```
cttccccttc agccaatcac cgttcgaggc ccgcccccgt cgccggaagg agccgtcgcc    60
ccgagcaact acaacgtccg gctttctgag ttgggtggcg ggaaaggcga tgagtaaagg   120
ccgggcagaa gctgcggcgg gagccgccgg gatcctcctg aggtacctgc aggagcagaa   180
ccggccctac agctcccagg atgtgttcgg gaacctacag cgggaacacg gactgggcaa   240
ggcggtggtg gtgaagacgc tggagcagct ggcgcaacaa ggcaagatca agagaagat    300
gtacggcaag cagaagatct attttgcgga tcaggaccac tttgacatga gctcaaggaa   360
ttatctagtg ccctgaccac accagagatg cagaaagaaa tccaggagtt aaagaaggaa   420
tgcgctggct acagagagag attgaagaac attaaagcag ctaccaatca tgtgactcca   480
gaagagaaag agcaggtgta cagagagagg cagaagtact gtaaggagtg gaggaagagg   540
aagaggatgg ctacagagct gtctgatgca atacttgaag ataccccaa gagcaagaag    600
cagttctttg aggaagttgg gatagagacg gatgaagatt acaacgtcac actcccagac   660
ccctgagggg cc                                                       672
```

<210> SEQ ID NO 11
<211> LENGTH: 761
<212> TYPE: DNA
<213> ORGANISM: Homo sapiens

<400> SEQUENCE: 11

```
gggaaaggcg atgagtaaag gccgggcaga agctgcggcg ggaggtaacg gcgccgtggg    60
cgcggggaag acccgggagg gcagtgggtg aggaggtcgg ttgagtggcc ccctcccctg   120
cctttctctc cgtagccgcc gggatcctcc tgaggtacct gcaggagcag aaccggccct   180
```

-continued

```
acagctccca ggatgtgttc gggaacctac agcgggaaca cggactgggc aaggcggtgg    240
tggtgaagac gctggagcag ctggcgcaac aaggcaagat caaagagaag atgtacggca    300
agcagaagat ctattttgcg gatcaggacc agtttgacat ggtgagtgat gctgaccttc    360
aagtcctaga tggcaaaatc gtggccctca ctgctaaggt gcagagcttg cagcagagct    420
gccgctacat ggaggctgag ctcaaggaat tatctagtgc cctgaccaca ccagagatgc    480
agaaagaaat ccaggagtta aagaaggaat gcgctggcta cagagagaga ttgaagaaca    540
ttaaagcagc taccaatcat gtgactccag aagagaaaga gcaggtgtac agagagaggc    600
agaagtactg taaggagtgg aggaagagga agaggatggc tacagagctg tctgatgcaa    660
tacttgaagg ataccccaag agcaagaagc agttctttga ggaagttggg atagagacgg    720
atgaagatta caacgtcaca ctcccagacc cctgaggggc c                        761
```

<210> SEQ ID NO 12
<211> LENGTH: 664
<212> TYPE: DNA
<213> ORGANISM: Homo sapiens

<400> SEQUENCE: 12

```
gggaaaggcg atgagtaaag gccgggcaga agctgcggcg ggaggtaacg gcgccgtggg     60
cgcggggaag acccgggagg gcagtgggtg aggaggtcgg ttgagtggcc ccctcccctg    120
cctttctctc cgtagccgcc gggatcctcc tgaggtacct gcaggagcag aaccggccct    180
acagctccca ggatgtgttc gggaacctac agcgggaaca cggactgggc aaggcggtgg    240
tggtgaagac gctggagcag ctggcgcaac aaggcaagat caaagagaag atgtacggca    300
agcagaagat ctattttgcg gatcaggacc agtttgacat gagctcaagg aattatctag    360
tgccctgacc acaccagaga tgcagaaaga aatccaggag ttaaagaagg aatgcgctgg    420
ctacagagag agattgaaga acattaaagc agctaccaat catgtgactc cagaagagaa    480
agagcaggtg tacagagaga ggcagaagta ctgtaaggag tggaggaaga ggaagaggat    540
ggctacagag ctgtctgatg caatacttga aggataccccc aagagcaaga agcagttctt    600
tgaggaagtt gggatagaga cggatgaaga ttacaacgtc acactcccag acccctgagg    660
ggcc                                                                 664
```

<210> SEQ ID NO 13
<211> LENGTH: 92
<212> TYPE: PRT
<213> ORGANISM: Homo sapiens

<400> SEQUENCE: 13

```
Met Gln Lys Glu Ile Gln Glu Leu Lys Lys Glu Cys Ala Gly Tyr Arg
1               5                   10                  15

Glu Arg Leu Lys Asn Ile Lys Ala Ala Thr Asn His Val Thr Pro Glu
            20                  25                  30

Glu Lys Glu Gln Val Tyr Arg Glu Arg Gln Lys Tyr Cys Lys Glu Trp
        35                  40                  45

Arg Lys Arg Lys Arg Met Ala Thr Glu Leu Ser Asp Ala Ile Leu Glu
    50                  55                  60

Gly Tyr Pro Lys Ser Lys Lys Gln Phe Phe Glu Glu Val Gly Ile Glu
65                  70                  75                  80

Thr Asp Glu Asp Tyr Asn Val Thr Leu Pro Asp Pro
                85                  90
```